United States Patent
Sun et al.

(10) Patent No.: US 12,029,776 B2
(45) Date of Patent: *Jul. 9, 2024

(54) COMPOSITION FOR TREATING CANCER AND USE AND MEDICAMENT THEREOF

(71) Applicant: NEWISH TECHNOLOGY (BEIJING) CO., LTD., Beijing (CN)

(72) Inventors: Zhongjie Sun, Beijing (CN); Hailong Qi, Beijing (CN); Ligong Chen, Beijing (CN); Huangfan Xie, Beijing (CN); Defang Liu, Beijing (CN); Xiao E. Yan, Beijing (CN); Weiwei Li, Beijing (CN); Xiaofang Wang, Beijing (CN)

(73) Assignee: NEWISH TECHNOLOGY (BEIJING) CO., LTD., Beijing (CN)

( * ) Notice: Subject to any disclaimer, the term of this patent is extended or adjusted under 35 U.S.C. 154(b) by 513 days.

This patent is subject to a terminal disclaimer.

(21) Appl. No.: 17/292,835

(22) PCT Filed: Aug. 19, 2020

(86) PCT No.: PCT/CN2020/109967
§ 371 (c)(1),
(2) Date: May 11, 2021

(87) PCT Pub. No.: WO2022/007135
PCT Pub. Date: Jan. 13, 2022

(65) Prior Publication Data
US 2022/0305072 A1    Sep. 29, 2022

(30) Foreign Application Priority Data

Jul. 6, 2020 (CN) .......................... 202010641456.1

(51) Int. Cl.
| A61K 38/00 | (2006.01) |
| A61K 38/17 | (2006.01) |
| A61K 38/18 | (2006.01) |
| A61P 35/00 | (2006.01) |
| A61K 31/351 | (2006.01) |

(52) U.S. Cl.
CPC .......... *A61K 38/005* (2013.01); *A61K 38/179* (2013.01); *A61K 38/1866* (2013.01); *A61P 35/00* (2018.01); *A61K 31/351* (2013.01)

(58) Field of Classification Search
None
See application file for complete search history.

(56) References Cited

U.S. PATENT DOCUMENTS

| 2014/0336129 A1 | 11/2014 | Weihua | |
| 2022/0313652 A1* | 10/2022 | Sun | A61K 31/517 |
| 2022/0323470 A1* | 10/2022 | Qi | A61K 31/506 |

FOREIGN PATENT DOCUMENTS

| CN | 104436194 A | 3/2015 | |
| CN | 105358173 | 2/2016 | |
| CN | 110430876 A | 11/2019 | |
| CN | 111150848 A | 5/2020 | |
| CN | 105358173 B | * 9/2022 | ........... A61K 31/422 |
| JP | 2016-520066 | 7/2016 | |
| JP | 2016-535591 | 11/2016 | |
| WO | WO 2019/232403 | 12/2019 | |
| WO | WO2020/068661 A1 | 4/2020 | |

OTHER PUBLICATIONS

National cancer institute, what is cancer? https://www.cancer.gov/about-cancer/understanding/what-is-cancer accessed on May 8, 2020 (Year: 2015).*
National cancer institute, cancer prevention, https://www.cancer.gov/about-cancer/causes-prevention/patient-prevention-overview-pdq accessed May 8, 2020 (Year: 2020).*
Merck manual, cancer treatment principles, by Robert Gale, https://www.merckmanuals.com/home/cancer/prevention-and-treatment-of-cancer/cancer-treatment-principles?query=Cancer%20treatment Accessed May 8, 2020 (Year: 2018).*
Merck manual, overview of cancer therapy, by Robert Gale, https://www.merckmanuals.com/professional/hematology-and-oncology/principles-of-cancer-therapy/overview-of-cancer-therapy?query=Cancer Accessed May 8, 2020 (Year: 2018).*
Medical news today by Christina Chun, https://www.medicalnewstoday.com/articles/322700 Accessed May, 8, 2020 (Year: 2018).*
Translation of CN105358173B provided by Espacenet (Year: 2016).*
Inoue et al. (Clin Cancer Res; 18(14) Jul. 15, 2012). Vandetanib, an Inhibitor of VEGF Receptor-2 and EGF Receptor, Suppresses Tumor Development and Improves Prognosis of Liver Cancer in Mice. (Year: 2012).*
Blessing et al., "Sodium/Glucose Co-transporter1 Expression Increases in Human Diseased Prostate," *J. Cancer Sci. Ther.*, 4(9):306-312, 2012.
Chang and Qi-zheng, "Research advance of VEGFR2 inhibitors as anti-angiogenic agents," *Chinese Journal of Antibiotics*, 43(6): 654-664, 2018. (English abstract of Chinese publication).
Ganapathy et al., "Nutrient transporters in cancer: relevance to Warburg hypothesis and beyond," *Pharmacology & Therapeutics* 121(1):29-40, 2009.
Giatromanolaki et al., "Hypoxia and activated VEGF/receptor pathway in multiple myeloma," *Anticancer Res.*, 30:2831-2836, 2010.
Hamerlik et al., "Autocrine VEGF-VEGFR2-neuropilin-1 signaling promotes glioma stem-like cell viability and tumor growth," *J. Exp. Med.*, 209:507-520, 2012.

(Continued)

*Primary Examiner* — Aradhana Sasan
*Assistant Examiner* — Mercy H Sabila
(74) *Attorney, Agent, or Firm* — Parker Highlander PLLC

(57) ABSTRACT

The present invention relates to the field of medical technology, in particular to a composition for treating cancer and use and medicament thereof. The composition comprises an SGLT1 inhibitor and a VEGFR2 inhibitor. The present invention finds that SGLT1 interacts with VEGFR2 to promote the development and progression of tumors; the present invention also finds that a composition of a VEGFR2 targeting inhibitor and an SGLT1 inhibitor has a synergistic anti-tumor effect, and the composition of the VEGFR2 targeting inhibitor and the SGLT1 targeting inhibitor can be used in cancer treatment.

5 Claims, 17 Drawing Sheets

Specification includes a Sequence Listing.

(56) References Cited

OTHER PUBLICATIONS

Hanahan et al., "Hallmarks of cancer: the next generation," *Cell*, 144(5):646-674, 2011.
Huang et al. "Prognostic significance and potential therapeutic target of VEGFR2 in hepatocellular carcinoma," *J. Clin. Pathol.*, 64:343-348, 2011.
Koepsell, "The Na+-D-glucose cotransporters SGLT1 and SGLT2 are targets for the treatment of diabetes and cancer," *Pharmacol. Ther.*, 170:148-65, 2017.
Kowanetz and Ferrara, "Vascular endothelial growth factor signaling pathways: therapeutic perspective," *Clin. Cancer Res.*, 12:5018-5022, 2006.
Leung et al., "Vascular endothelial growth factor is a secreted angiogenic mitogen," *Science*, 246:1306-1309, 1989.
Madunić et al., "Apigenin: A dietary flavonoid with diverse anti-cancer properties," *Cancer Lett.*, 413:11-22, 2018.
Shixiong et al., "Expression and significance of SGLT1 in human liver cancer," *Modern Oncology*, 23(3):354-356, 2015. (English abstract of Chinese publication).
Thorens and Mueckler, "Glucose transporters in the 21st Century," *Am. J. Physiol-Endoc. M.*, 298:E141-5, 2010. doi:10.1152/ajpendo. 00712.2009.
Tischer et al. "Vascular endothelial growth factor: a new member of the platelet-derived growth factor gene family," *Biochem Biophys Res Commun.*, 165:1198-1206, 1989.
Waldner et al., "VEGF receptor signaling links inflammation and tumorigenesis in colitis associated cancer," *J. Exp. Med.*, 207:2855-2868, 2010.
Wang et al., "Study on the expression and effect of sodium-glucose transporter 1 in ovarian cancer," *China Maternal and Child Health Care*, 29:3144-3147, 2014. (English abstract of Chinese publication).
Wang et al., "The roles of sodium-glucose transporters in tumor cell energy metabolism," *J. Clin. Otorhinolaryngol. Head Neck Surgery (China)*, 31(6):482-486, 2017. (English abstract of Chinese publication).
Weihua et al., "Survival of cancer cells is maintained by EGFR independent of its kinase activity," *Cancer Cell*, 13(5):385-393, 2008.
Wilson et al., "Intratumoral expression profiling of genes involved in angiogenesis in colorectal cancer patients treated with chemotherapy plus the VEGFR inhibitor PTK787/ZK 222584 (vatalanib)," *The Pharmacogenomics Journal*, 13:410-416, 2013.
Wright et al., "Biology of human sodium glucose transporters," *Physiological Reviews*, 912:733-794, 2011.
Yamazaki et al., "Sodium-glucose transporter as a novel therapeutic target in disease," *Eur. J. of Pharmacol.*, 822:25-31, 2018.
Zhang et al., "A sodium-glucose cotransporter 2 inhibitor attenuates renal capillary injury and fibrosis by a vascular endothelial growth factor-dependent pathway after renal injury in mice," *Kidney International*, 94:524-535, 2018.
Office Communication issued in correspondence Japanese Application No. 2021-525310 dated Oct. 24, 2022 {English translation}.
Office Communication issued in correspondence Chinese Application No. 202010641456.1 dated Oct. 31, 2022 {English translation and original}.
Extended European Search Report issued in International Application No. PCT/CN2020/109966, dated Jan. 26, 2022.
Meadows KL, Hurwitz HI. Anti-VEGF therapies in the clinic. Cold Spring Harb Perspect Med. Oct. 1, 2012:2(10):a006577. doi: 10.1101/cshperspect.a006577. PMID: 23028128; PMCID: PMC3475399.
Tabernero J. The role of VEGF and EGFR inhibition: implications for combining anti-VEGF and anti-EGFR agents. Molecular Cancer Research : MCR. Mar. 2007;5(3):203-220. DOI: 10.1158/1541-7786.mcr-06-0404. PMID: 17374728.
Office Action issued in Chinese Application No. 2020106414561, dated Apr. 26, 2022, English Translation included.

\* cited by examiner 2A　　2B

Control group

Knocking down VEGFR2

Knocking down SGLT1

Knocking down SGLT2

The medication effects of apatinib in combination with different concentrations of sotagliflozin (S) on the liver cancer HepG2 cell line The medication effects of apatinib in combination with different concentrations of sotagliflozin (S) on the colorectal adenocarcinoma SW620 cell line The medication effects of apatinib in combination with different concentrations of sotagliflozin (S) on the cervical cancer Hela cell line The medication effects of apatinib in combination with different concentrations of sotagliflozin (S) on the ovarian cancer SKOV3 cell line The medication effects of apatinib in combination with different concentrations of sotagliflozin (S) on the gastric cancer NGC-27 cell line The medication effects of apatinib in combination with different concentrations of sotagliflozin (S) on the cholangiocarcinoma RBE cell line The medication effects of apatinib in combination with different concentrations of sotagliflozin (S) on the esophagus cancer KYSE30 cell line

COMPOSITION FOR TREATING CANCER AND USE AND MEDICAMENT THEREOF

This application is the national phase of International Application No. PCT/CN2020/109967, titled "COMPOSITION FOR TREATING CANCER AND USE AND MEDICAMENT THEREOF", filed on Aug. 19, 2020, which claims the priority to Chinese Patent Application No. 202010641456.1 filed with the China National Intellectual Property Administration on Jul. 6, 2020 and titled "COMPOSITION FOR TREATING CANCER AND USE AND MEDICAMENT THEREOF", the content of which is incorporated herein by reference in its entirety.

Pursuant to 37 C.F.R. 1.821(c), a sequence listing is submitted herewith as an ASCII compliant text file named "UNITP0055US_ST25.txt", created on May 10, 2021 and having a size of ~2 KB kilobytes. The content of the aforementioned file is hereby incorporated by reference in its entirety.

FIELD

The present invention relates to the field of medical technology, in particular to a composition for treating cancer and use and medicament thereof.

BACKGROUND

Malignant tumors are one of the main diseases threatening human life in today's society. Tumor growth and invasion need to induce neoangiogenesis. The most important factor in neoangiogenesis induction is vascular endothelial growth factor (VEGF). VEGF secreted by tumor cells binds with a vascular endothelial growth factor receptor (VEGFR) to promote vascular endothelial cell proliferation and division to form new blood vessels thereby promoting tumor growth (Leung D W, Cachianes G, Kuang W J, Goeddel D V, Ferrara N. Vascular endothelial growth factor is a secreted angiogenic mitogen. Science. 1989; 246:1306-1309. Tischer E, et al. Vascular endothelial growth factor: a new member of the platelet-derived growth factor gene family. Biochem Biophys Res Commun. 1989; 165:1198-1206.). Therefore, targeting the activity of VEGFR tyrosine kinase with small molecules to inhibit tumor neoangiogenesis thereby starving the tumor has become a new approach for tumor treatment in recent years. However, targeting VEGFR via small molecule inhibitors of receptor tyrosine kinases has not produced satisfactory therapeutic efficacy. The overall response rate of various human malignant tumors is low, and problems such as rapid development of drug resistance need to be solved urgently.

There are three main members of the VEGFR family: VEGFR1, VEGFR2, and VEGFR3, among which VEGFR2 mainly mediates the growth of vascular endothelial cells. Recent studies have shown that VEGFR2 is also highly expressed in some tumor cells. Therefore, VEGF secreted by the tumor cells induces neoangiogenesis while acting on the tumor cells themselves or adjacent tumor cells or mesenchymal cells in a way of autocrine or paracrine to promote the formation of tumor stem cells and immune tolerance microenvironment (Kowanetz M, Ferrara N. Vascular endothelial growth factor signaling pathways: therapeutic perspective. Clin Cancer Res. 2006; 12:5018-5022. Waldner M J, et al. VEGF receptor signaling links inflammation and tumorigenesis in colitis associated cancer. J Exp Med. 2010; 207:2855-2868. Hamerlik P, et al. Autocrine VEGF-VEGFR2-neuropilin-1 signaling promotes glioma stem-like cell viability and tumor growth. J Exp Med. 2012; 209:507-520.). However, the specific mechanism of VEGFR binding with the ligand thereby promoting the proliferation and survival of the tumor cells themselves as well as cancer development is still poorly understood.

A sign that tumor cells are different from normal cells is that they preferentially use aerobic glycolysis to provide energy for themselves even under conditions of sufficient oxygen. Compared with oxidative phosphorylation, aerobic glycolysis has a much lower energy-producing efficiency, which requires a significant increase in the ability of tumor cells to transport glucose (Hanahan D et al, Hallmarks of cancer: the next generation, Cell, 144(5):646-674(2011)), and this is achieved by overexpression of plasma membrane transporters (Ganapathy V, et al, Nutrient transporters in cancer: relevance to Warburg hypothesis and beyond, Pharmacology & Therapeutics 121(1):29-40(2009)). Sodium/glucose co-transporter 1 (SGLT1) is an active glucose transporter, which transports glucose to cells relying on extracellular sodium concentration rather than glucose concentration (Wright E M, et al, Biology of human sodium glucose transporters, Physiological Reviews, 91(2):733-794 (2011)). Studies have shown that SGLT1 is highly expressed in a variety of cancers and is associated with their poor prognosis, these cancers includes ovarian cancer, oral squamous cell carcinoma, colorectal adenocarcinoma, pancreatic cancer and prostate cancer. SGLT1 can bind to and stabilize EGFR to promote the growth and proliferation of tumor cells (Madunić J, Vrhovac Madunić I, Gajski G, Popić J, GarajVrhovac V. Apigenin: A dietary flavonoid with diverse anticancer properties. Cancer Lett 2018; 413:11-22. Koepsell H. The Na+ −D-glucose co-transporters SGLT1 and SGLT2 are targets for the treatment of diabetes and cancer. Pharmacol Ther 2017; 170:148-65. Yamazaki Y, Harada S, Tokuyama S. Sodium-glucose transporter as a novel therapeutic target in disease. Eur J of Pharmacol 2018; 822:25-31).

At present, there are no reports of using an SGLT1 inhibitor in combination with a VEGFR2 inhibitor for solving the problem of treating cancers resistant to VEGFR tyrosine kinase inhibitors in this field.

SUMMARY

In view of this, the present invention provides a composition for treating cancer and use and medicament thereof. The present invention finds that SGLT1 interacts with VEGFR2 to promote the development and progression of tumors, and a composition of the VEGFR2 targeting inhibitor and the SGLT1 inhibitor has a synergistic anti-tumor effect.

In order to achieve the above-mentioned invention object, the present invention provides the following technical solutions:

The present invention provides a composition comprising a sodium/glucose co-transporter 1 (SGLT1) inhibitor and a vascular endothelial growth factor receptor (VEGFR) inhibitor. Preferably, the active ingredients consist of the SGLT1 inhibitor and the VEGFR2 inhibitor.

As a preference, the SGLT1 inhibitor is selected from, but not limited to, at least one of sotagliflozin, mizagliflozin, KGA-2727, canagliflozin and dapagliflozin, and the SGLT1 inhibitors considered feasible by those skilled in the art are all within the protection scope of the present invention.

As a preference, the SGLT1 inhibitor is administered at a dosage of 1 to 100 mg/kg.

Preferably, the SGLT1 inhibitor is administered at a dosage of 10 to 50 mg/kg.

As a preference, the VEGFR2 inhibitor is selected from at least one of apatinib, axitinib, nintedanib (BIBF 1120), cediranib (AZD2171), pazopanib HCl (GW786034 HCl), sunitinib malate, brivanib (BMS-540215), cabozantinib (XL184, BMS-907351), brivanib alaninate (BMS-582664), lenvatinib (E7080), regorafenib (BAY 73-4506), ENMD-2076, tivozanib (AV-951), ponatinib (AP24534), ENMD-2076 L-(+)-tartaric acid, telatinib, taxifolin (dihydroquercetin), pazopanib, cabozantinib malate (XL184), vitamin E, regorafenib monohydrate, nintedanib ethanesulfonate salt, levatinib mesylate, cediranib maleate, fruquintinib, 4-[(1E)-2-[5-[(1R)-1-(3,5-dichloro-4-pyridyl)ethoxy]-1H-indazol-3-yl]vinyl]-1H-pyrazole-1-etha nol (LY2874455), sunitinib, sitravatinib (MGCD516), anlotinib (AL3818) dihydrochloride, sorafenib, vandetanib, and a monoclonal antibody targeting VEGFR.

A VEGFR-targeting monoclonal antibody is, for example, bevacizumab, but is not limited to this. The VEGFR-targeting monoclonal antibodies considered feasible by those skilled in the art are all within the protection scope of the present invention.

As a preference, the VEGFR2 inhibitor is administered at a dosage of 10 to 500 mg/kg.

Preferably, the VEGFR2 inhibitor is administered at a dosage of 10 to 100 mg/kg.

The invention also provides use of the composition in the manufacture of a medicament for treating cancer.

As a preference, the cancer includes: bladder cancer, blood cancer, bone cancer, brain cancer, breast cancer, central nervous system cancer, cervical cancer, colon cancer, endometrial cancer, esophageal cancer, gallbladder cancer, gastrointestinal tract cancer, external genital cancer, genitourinary tract cancer, head cancer, kidney cancer, laryngeal cancer, liver cancer, lung cancer, muscle tissue cancer, neck cancer, oral or nasal mucosal cancer, ovarian cancer, pancreas cancer, prostate cancer, skin cancer, spleen cancer, small intestine cancer, large intestine cancer, gastric cancer, testicular cancer and/or thyroid cancer.

The present invention also provides a medicament for treating cancer comprising the above-mentioned composition.

As a preference, the drug is administered orally, and the dosage form thereof includes granules, pills, powders, tablets, capsules, oral liquids or syrups.

As a preference, the drug is administered by injection, and the dosage form thereof includes injection liquids or injection powders.

The invention provides a composition for treating cancer and use and medicament thereof. The composition comprises an SGLT1 inhibitor and a VEGFR2 inhibitor. The technical effects of the present invention are as follows.

The present invention finds that SGLT1 interacts with VEGFR2 to promote the development and progression of tumors, and this interaction plays an important role in each other's functions. Knockdown of VEGFR2 will affects not only tumor cell proliferation and growth signal transduction, but also SGLT1 function; on the other hand, knockdown of SGLT1 affects not only the survival of cancer cells under low-glucose conditions, but also the VEGFR2 signaling pathway and cell proliferation;

The present invention also finds that the composition of the VEGFR2 targeting inhibitor and the SGLT1 inhibitor has a synergistic anti-tumor effect and can be used for cancer treatment.

BRIEF DESCRIPTION OF DRAWINGS

FIG. 1 shows that the high expression of VEGFR2 and that of SGLT1 are associated with poor prognosis of patients with liver cancer or colorectal adenocarcinoma; in which

FIG. 2 shows that VEGFR2 and SGLT1 are positively correlated in liver cancer and colorectal adenocarcinoma; in which FIG. 2A shows that the expression of VEGFR2 and that of SGLT1 are positively correlated in liver cancer, and FIG. 2B shows that the expression of VEGFR2 and that of SGLT1 are positively correlated in colorectal adenocarcinoma.

FIG. 10 shows the efficacy of the VEGFR2 inhibitor and the SGLT1 inhibitor for the treatment of the transplanted tumor of hepatocellular carcinoma in nude mice.

FIG. 11-1 to FIG. 11-30 respectively show the tumor suppression effect of axitinib (FIG. 11-1), nintedanib (FIG. 11-2), cediranib (FIG. 11-3), pazopanib HCl (FIG. 11-4), sunitinib malate (FIG. 11-5), brivanib (FIG. 11-6), cabozantinib (FIG. 11-7), brivanib alaninate (FIG. 11-8), lenvatinib (FIG. 11-9), regorafenib (FIG. 11-10), ENMD-2076 (FIG. 11-11), tivozanib (FIG. 11-12), ponatinib (FIG. 11-13), ENMD-2076 L-(+)-tartaric acid (FIG. 11-14), telatinib (FIG. 11-15), taxifolin (FIG. 11-16), pazopanib (FIG. 11-17), cabozantinib malate (FIG. 11-18), vitamin E (FIG. 11-19), regorafenib monohydrate (FIG. 11-20), nintedanib ethanesulfonate salt (FIG. 11-21), lenvatinib mesylate (FIG. 11-22), cediranib maleate (FIG. 11-23), 4-[(1E)-2-[5-[(1R)-1-(3,5-dichloro-4-pyridyl)ethoxy]-1H-indazol-3-yl]vinyl]-1H-pyrazole-1-etha nol (FIG. 11-24), sunitinib (FIG. 11-25), sitravatinib (FIG. 11-26), anlotinib dihydrochloride (FIG. 11-27), sorafenib (FIG. 11-28), vandetanib (FIG. 11-29) or fruquintinib (FIG. 11-30) in combination with the SGLT1 inhibitor sotagliflozin.

DETAILED DESCRIPTION

Figure 1A:
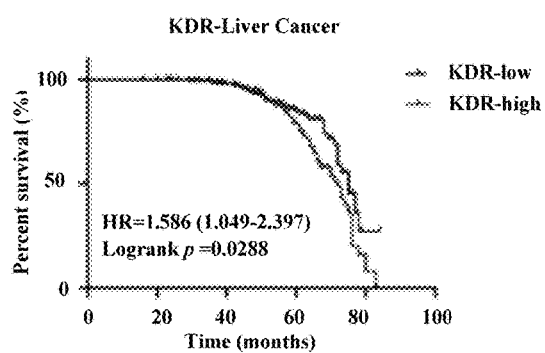
FIG. 1A is the relationship between high expression of VEGFR2 and the prognosis of patients with liver cancer.

The present invention discloses a composition for treating cancer and use and medicament thereof, and those skilled in the art can learn from the content of the present invention and appropriately improve the process parameters for achievement. It should be pointed out particularly that all similar substitutions and modifications are obvious to those skilled in the art, and they are all deemed to be included in the present invention. The methods and use of the present invention have been described through the preferred examples, and it is obvious that relevant persons can make changes or appropriate alterations and combinations to the methods and use described herein without departing from the content, spirit and scope of the present invention to achieve and apply the technology of the present invention.

According to TCGA data analysis, the poor prognosis of malignant tumors is related to the overexpression of vascular endothelial growth factor receptor 2 (VEGFR2) and sodium/glucose co-transporter 1 (SGLT1). The cancer includes liver cancer, breast cancer, colorectal adenocarcinoma. The present invention finds that VEGFR interacts with SGLT1 in cancer cells to affect each other's functions.

Through the following numerous detailed description, the following embodiments have been determined in the present invention:

1) The effect of the high expression of VEGFR2, SGLT1 and SGLT2 in liver cancer and breast cancer on the poor prognosis of cancer patients;

2) The effect of SGLT1 on the VEGFR2 signaling pathway;

3) The inhibitory effect of SGLT1 on the sensitivity of the VEGFR2 tyrosine inhibitor in liver cancer cells;

4) The effect of VEGFR2 on the normal function of SGLT1;

5) The interaction between VEGFR2 and SGLT1;

6) The effect of the VEGFR2 inhibitor and the SGLT1 inhibitor used as single agents or a composition thereof on tumor cells;

7) The effect of the VEGFR2 inhibitor and the SGLT1 inhibitor used as single agents or a composition thereof on the transplanted tumor in nude mice.

The test results of the present invention are as follows:

(1) The high expression of VEGFR2 and that of SGLT1 are positively correlated, which is positively correlated with the poor prognosis of cancer patients In one embodiment, the high expression of VEGFR2 and SGLT1 in patients with liver cancer or breast cancer is positively correlated with poor prognosis, and the high expression of VEGFR2 is also positively correlated with that of SGLT1. In another embodiment, knockdown of SGLT1 damages the VEGFR2 signaling while enhancing the sensitivity of the corresponding tumor cell line to VEGFR2 tyrosine kinase activity inhibitors. In another embodiment, knockdown of VEGFR2 also damages the function of SGLT1, and there is a direct interaction between SGLT1 and VEGFR2. All these data show that the expression of VEGFR2 and vascular endothelial cells can promote neoangiogenesis and tumor progression, and the expression thereof in the tumor cells themselves can regulate the energy metabolism and proliferation signals of the tumor cells through interaction with SGLT1. Therefore, in an embodiment, SGLT1 is a protein involved in the function of VEGFR2, and the VEGFR2-SGLT1 interaction may be a novel target for cancer treatment.

Figure 1B:
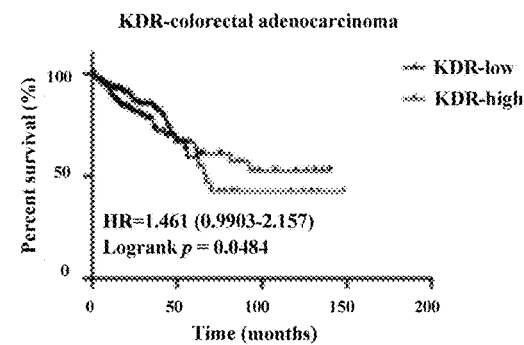
FIG. 1B is the relationship between high expression of VEGFR2 and the prognosis of patients with colorectal adenocarcinoma.

Studies have shown that VEGFR2 is highly expressed not only in vascular endothelial cells but also in certain cancer cells themselves. It is clear that SGLT1 is highly expressed in prostate cancer (Huang J, et al. Prognostic significance and potential therapeutic target of VEGFR2 in hepatocellular carcinoma. J Clin Pathol. 2011; 64:343-348. Blessing A, et al. Sodium/Glucose Co-transporter1 Expression Increases in Human Diseased Prostate, J. Cancer Sci. Ther. 4(9):306-312(2012)). By performing survival analysis for the expression level of VEGFR2, SGLT1 and SGLT2 and the overall survival of patients with liver cancer or colorectal adenocarcinoma according to the study on the TCGA database, the present invention has found that, the high expression of VEGFR2 and SGLT1 is positively correlated with poor prognosis in patients with liver cancer or colorectal adenocarcinoma, while SGLT2 has no such correlation. As shown in FIGS. 1A and 1B, it is demonstrated illustratively that the high expression of VEGFR2 and SGLT1 is correlated to the poor prognosis of patients with either of these two kinds of cancer, indicating the relationship between their expression in the tumor cells themselves and the prognosis. This is not intended to limit the composition of the embodiments of the present invention for liver cancer or colorectal adenocarcinoma only. For example, in another embodiment, the composition has a significant inhibitory effect on the cervical cancer, ovarian cancer, gastric cancer, esophageal cancer, or cholangiocarcinoma cell line, as shown in FIG. 9b-9f.

Further in another embodiment, by performing correlation analysis on data of the expression level of VEGFR2 and SGLT1, SGLT2 in patients with liver cancer or breast cancer tumor obtained from the TCGA database using Pearson's test, the present invention has found that there is a positive correlation between VEGFR2 and SGLT1 expression, but no correlation between VEGFR2 and SGLT2 expression, as shown in FIGS. 2A and 2B. This shows that the function of VEGFR2 and that of SGLT1 are likely to have a certain correlation. In order to verify the importance of VEGFR2 and SGLT1 for liver cancer as shown by TCGA data, the present invention knocked down VEGFR2 and SGLT1 in the liver cancer cell line Hep3B respectively and performed experiments on the transplanted tumor in nude mice, and found that the tumorigenicity of the transplanted tumor of the cell line in which VEGFR2 or SGLT1 was knocked down in nude mice is significantly reduced, indicating that these two genes play an important role in the development and progression of tumors, as shown in FIG. 3.

(2) VEGFR2 and SGLT1 affect each other's functions

Figure 4:
FIG. 4 shows that knockdown of SGLT1 damages the VEGFR2 signaling pathway. P-ERK1/2 is used as a marker to indicate the strength of the VEGFR2 signaling pathway in the present invention.
Figure 4:
Figure 5:
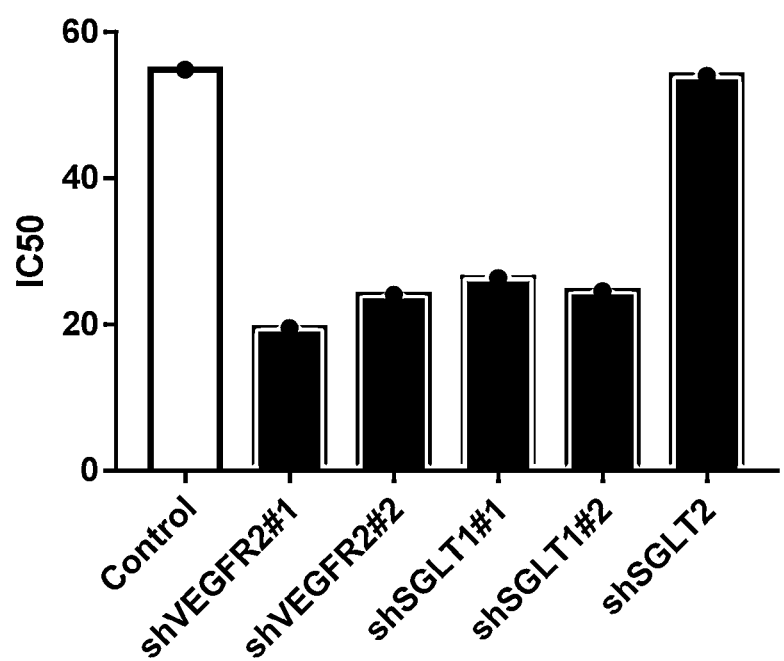
FIG. 5 shows that knockdown of VEGFR2 or SGLT1 increases the sensitivity of the liver cancer cell line Hep3B to apatinib.
Figure 6:
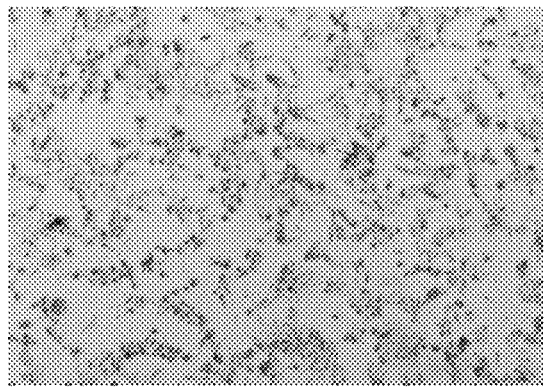
FIG. 6 shows that knockdown of VEGFR2 or SGLT1 increases the sensitivity of Hep3B cells to glucose starvation.
Figure 6:
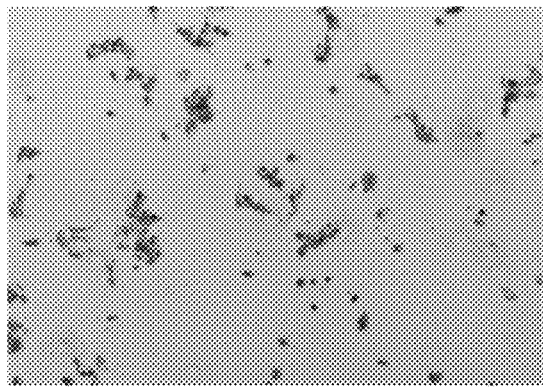
Figure 6:
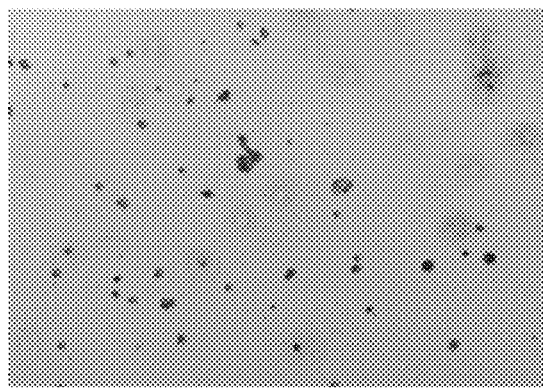
Figure 6:
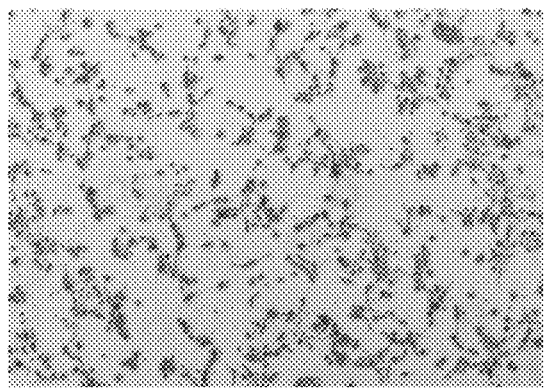

According to the inference derived from the foregoing data analysis of the present invention, in an embodiment, the present invention uses lentivirus to infect cells, and uses shRNA technology to knock down VEGFR2, SGLT1 and SGLT2 in liver cancer Hep3B cells respectively to verify the functional mutual influence between one another. ERK1/2 is a downstream molecule after activation of VEGFR2 tyrosine kinase activity. VEGFR2 activation will cause phosphorylation of ERK1/2 (Giatromanolaki A, et al. Hypoxia and activated VEGF/receptor pathway in multiple myeloma. Anticancer Res. 2010; 30:2831-2836.). In an embodiment, the present invention evaluates the intensity of phosphorylated ERK1/2 after knockdown of VEGFR2, SGLT1 and SGLT2 to determine whether knockdown of SGLT1/2 affects the VEGFR2 signal. The results are shown in FIG. 4, knockdown of SGLT1 and of VEGFR2 will consistently induce the down-regulation of the intensity of phosphorylation of ERK1/2, while knockdown of SGLT2 has no such effect. If knockdown of SGLT1 causes damage to the VEGFR2 signaling pathway, the corresponding cells in which SGLT1 is knocked down will be more sensitive to the VEGFR2 inhibitor, just like cells in which VEGFR2 is knocked down. Taking the VEGFR2 inhibitor apatinib as an example only, the present invention is performed by placing the control cells and each cell line in which VEGFR2, SGLT1 or SGLT2 is knocked down on a 96-well plate, adding different concentrations of apatinib for the treatment of each group of cells. The IC50 values of apatinib on each group of cells are measured by MTT method. The results are shown in FIG. 5, knockdown of SGLT1 and of VEGFR2 consistently reduced the IC50 value of apatinib by more than half, while knockdown of SGLT2 had no such effect. It is well known that SGLT1 provides energy for cells to absorb glucose from the external environment against the glucose concentration gradient (Thorens B, Mueckler M. Glucose transporters in the $21^{st}$ Century. Am J Physiol-Endoc M 2010; 298: E141-5. doi:10.1152/ ajpendo.00712.2009). Therefore, tumor cells in which SGLT1 is knocked down will preferentially die due to lack of glucose supply under low-glucose culture conditions. In an embodiment of the present invention, liver cancer Hep3B cells in which VEGFR2, SGLT1 or SGLT2 was knocked down were cultured using a low-glucose medium, and the cell status was observed at regular intervals under a light microscope. The results are shown in FIG. 6. Knockdown of VEGFR2 and that of SGLT1 consistently reduced the tolerance of cells to glucose starvation, while knockdown of SGLT2 had no significant effect. Based on the above, the present invention found for the first time that there is a functional mutual influence between the two molecules of VEGFR2 and SGLT1.

It is worth mentioning that the present invention only takes liver cancer Hep3B cells as an example to knock down each gene to evaluate their mutual influence, and the conclusions of the present invention should not be limited to this cancer type and cell line.

(3) There is an intermolecular interaction between VEGFR2 and SGLT1

Figure 7:
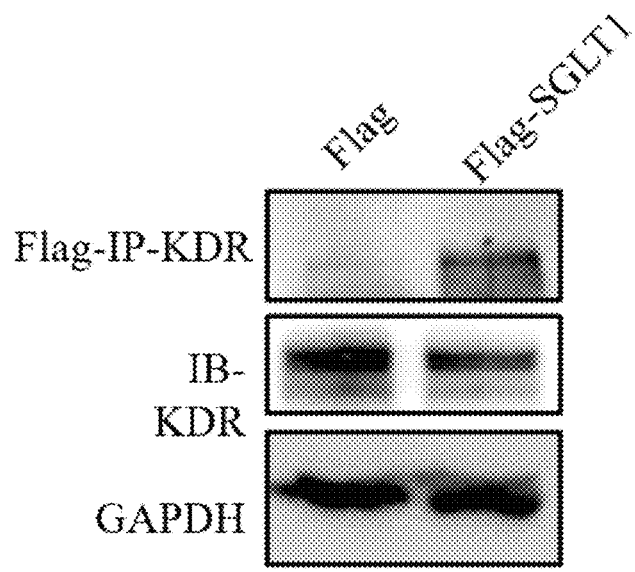
FIG. 7 shows that there is an interaction between VEGFR2 and SGLT1 proteins.

Based on the functional mutual influence between VEGFR2 and SGLT1, which is found for the first time in the present invention, in an embodiment of the present invention, the intermolecular interaction between VEGFR2 and SGLT1 is further determined through an immunoprecipitation experiment. HEK293T cells were transfected with the plasmid expressing Flag-tagged SGLT1 alone or in admixture with the designated GFP-tagged VEGFR2 vector in serum-free DMEM medium with the transfection reagent PEI added. 6 hours after transfection, the medium was changed to 10% serum medium. 24 hours after changing the medium, the medium was discarded and the cells were washed with 10 ml of 1× phosphate buffered saline (PBS) and then blowed up and centrifuged at 1500 rpm. The supernatant was discarded and RIPA buffer (50 mM Tris-HCl, pH 8.0, with 150 mM sodium chloride, 1.0% Igepal CA-630(NP-40), 0.5% sodium deoxycholate and 0.1% sodium dodecylsulfate) supplemented with a protease inhibitor mixture was added to the resultant cell pellet deposit and lysis was performed on a shaker at 4° C. for 30 minutes. Then, the cell lysate was centrifuged at 12000× rpm for 10 minutes. M2 microbeads coupled with Flag antibody were added to the supernatant and incubation was performed overnight at 4° C. Then, the samples were centrifuged, washed three times with RIPA buffer, boiled in Laemmle buffer (Biorad, CA), and western blot analysis was preformed using 8% SDS PAGE gel. IP=immunoprecipitation, IB=immunoblotting, and Input=the expression level of the specified foreign protein in the HEK293 whole cell lysate used for immunoprecipitation. The result is shown in FIG. 7.

(4) Inhibition of SGLT1 by the SGLT1 inhibitor makes liver cancer or colorectal adenocarcinoma cells sensitive to the VEGFR2 inhibitor.

Figure 8:
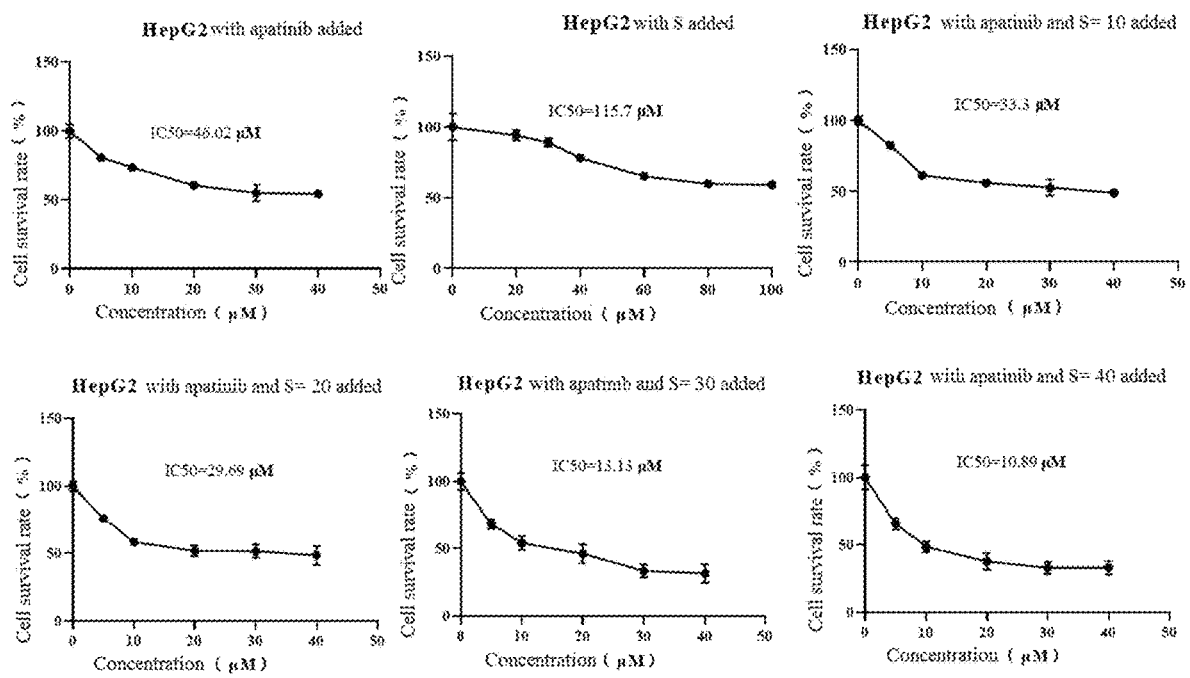
FIG. 8 shows the treatment of the hepatoma cell line HepG2 with the VEGFR2 inhibitor and the SGLT1 inhibitor.
Figures 1, 11:
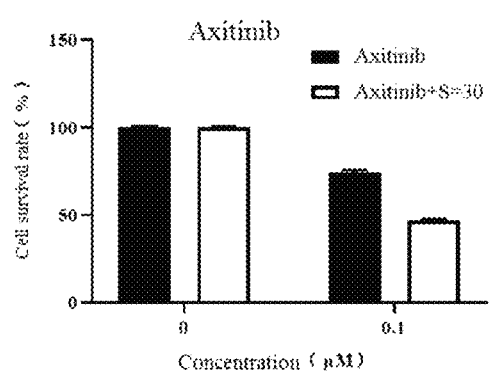
Figures 2, 11:
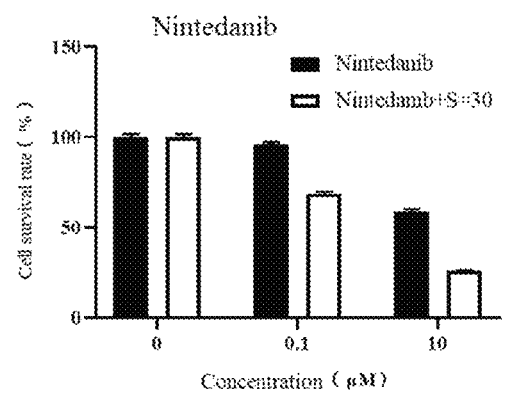
Figures 3, 11:
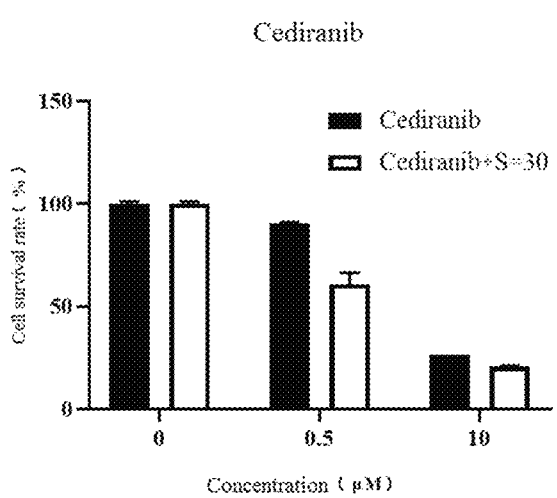
Figures 4, 11:
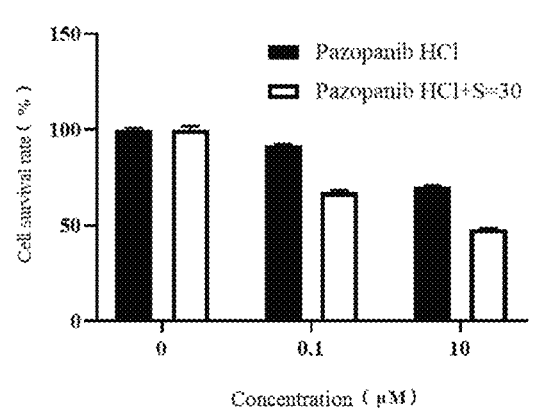
Figures 5, 11:
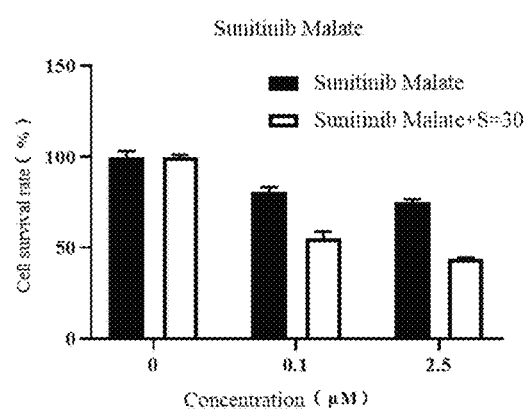
Figures 6, 11:
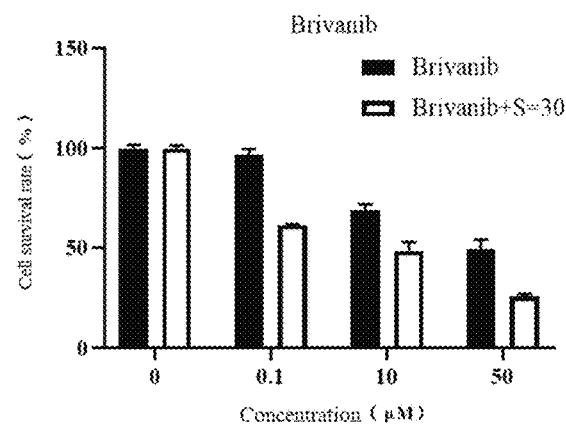
Figures 7, 11:
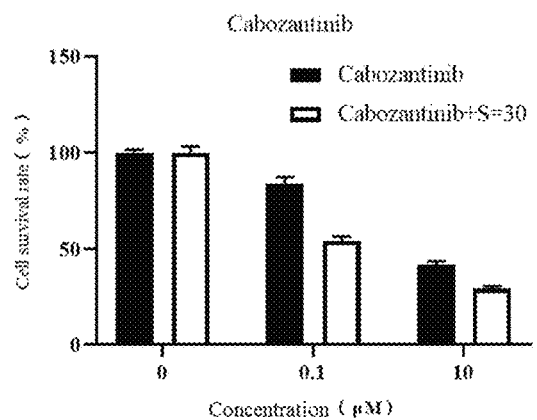
Figures 8, 11:
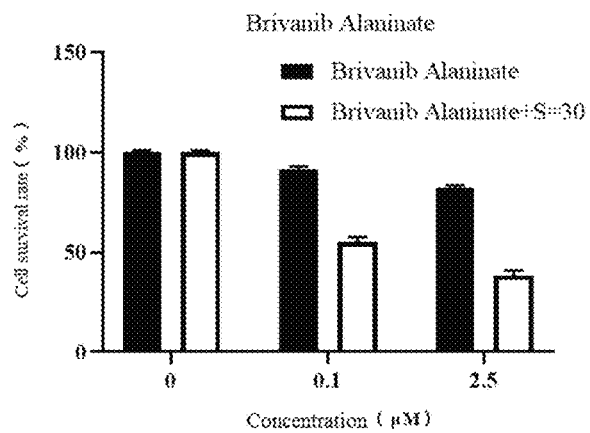
Figures 9, 11:
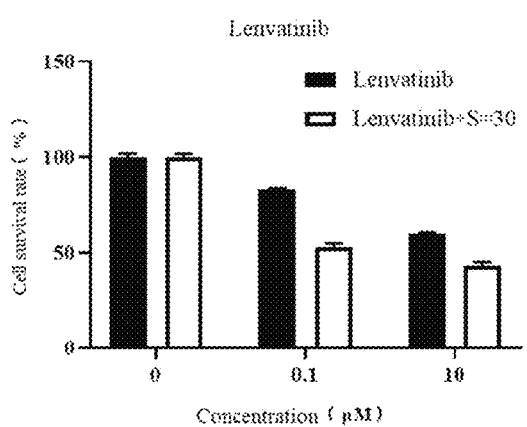
Figures 10, 11:
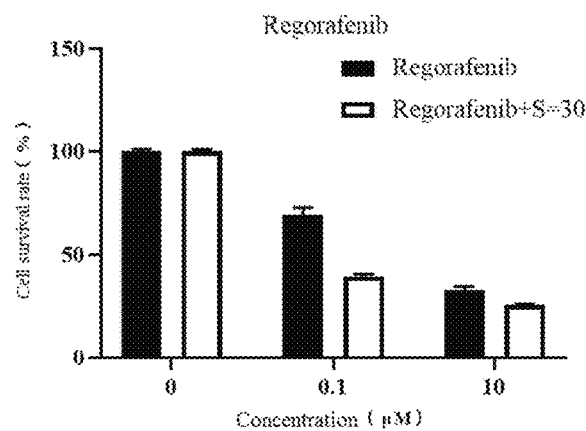
Figure 11:
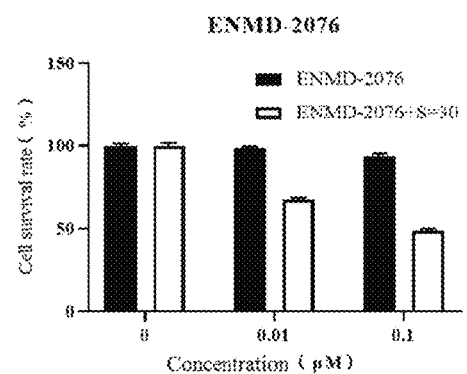

FIGS. 8 and 9 only demonstrate illustratively the evaluation of the IC50 values of the VEGFR2 inhibitor apatinib and the SGLT1 inhibitor sotagliflozin used as either single agents or a composition thereof in the liver cancer HepG2 cell line, the colorectal adenocarcinoma cell line SW620, and 5 other common cancer cell lines. Based on these results, in one embodiment, co-inhibition of SGLT1 and VEGFR2 function can more effectively inhibit the growth of cancer cells. In another embodiment, an SGLT1 inhibitor, such as sotagliflozin, can significantly allow the transplanted tumor of the liver cancer cell line Hep3B in nude mice sensitive to the growth inhibitory effect of apatinib, as shown in FIG. 10. In an embodiment, SGLT1 inhibitor compounds such as sotagliflozin can be administered intravenously or orally to patients to treat cancer. In another embodiment, SGLT1 inhibitor compounds such as sotagliflozin can be administered to patients together with a VEGFR2 tyrosine kinase inhibitor to treat cancer.

The reagents or instruments used in the composition for treating cancer and the use and medicament thereof provided by the present invention can be purchased from the market.

The present invention will be further illustrated in combination with the following examples.

Example 1

1. Cells and Reagents

Liver cancer cell lines Hep3B and HepG2; colorectal adenocarcinoma cell lines SW620, HCT116, SW480, LOVO, HT29 and DLD1; cervical cancer HeLa; ovarian cancer SKOV3; gastric cancer NGC27; cholangiocarcinoma RBE; esophageal cancer KYSE30 and HEK293T cell lines used in the present invention were all purchased from the American Type Culture Collection (ATCC) and cultured in a 37° C. incubator containing 5% $CO_2$, the maintenance medium of the cell lines is DMEM or RPMI 1640 (Gibco) supplemented with 10% fetal bovine serum (Gibco) and 1% penicillin/streptomycin (Gibco). Mouse anti-Flag tag antibody (F3165) and Flag antibody-coupled M2 microbeads were purchased from Sigma-Aldrich (St. Louis, MO). Mouse anti-GFP tag antibody, rabbit GAPDH internal reference antibody and horseradish peroxidase-labeled anti-rabbit and anti-mouse secondary antibodies were purchased from Beijing Biodragon Immunotechnologies Co., Ltd. Sotagliflozin, apatinib and lenvatinib were all obtained from Selleckchem (Houston, TX). Anti-pERK antibody (4370) was obtained from Cell Signaling (Danvers, MA). The MTT kit (catalog No. 30-1010K) was obtained from ATCC.

2. Plasmid Construction

The human wild-type VEGFR was cloned into the PEGFP-N1 vector, and the human wild-type SGLT1 sequence was cloned into the PCDH-EF1-CMV vector. The shRNAs targeting the following sequences were constructed into the pLVX-shRNA2-puro vector for subsequent lentivirus coating to construct cell lines in which SGLT1, SGLT2, or VEGFR2 is knocked down: Sglt1-1 shRNA sequence: 5'-AGGAGAGCCTATGACCTATTT-3' (SEQ ID NO: 1); Sglt1-2 shRNA sequence: 5'-GCCTGATGCTATCAGT-CATGC-3' (SEQ ID NO: 2); Sglt2-1 shRNA sequence: 5'-GCATATTTCCTGCTGGTCATT-3' (SEQ ID NO: 3); Sglt2-2 shRNA sequence: 5'-GGTCATCACGATGC-CACAGTA-3' (SEQ ID NO: 4); Vegfr2-1 shRNA sequence: 5'-GATGAAAGTTACCAGTCTATT-3' (SEQ ID NO: 5); Vegfr2-2 shRNA sequence: 5'-GCTGACATGTACGGTC-TATGC-3' (SEQ ID NO: 6). All vectors were verified as correct plasmids by sequencing.

3. Transient Transfection and Immunoprecipitation

HEK293T cells were transfected with the plasmid expressing Flag-tagged SGLT1 alone or in admixture with the designated GFP-tagged VEGFR2 vector in serum-free DMEM medium in which the transfection reagent PEI was added. 6 hours after transfection, the medium was changed to a 10% serum medium. 24 hours after changing the medium, the medium was discarded and the cells were washed with 10 ml of 1× phosphate buffered saline (PBS) and then blowed up and centrifuged at 1500 rpm. The supernatant was discarded and RIPA buffer (50 mM Tris-HCl, pH 8.0, with 150 mM sodium chloride, 1.0% Igepal CA-630(NP-40), 0.5% sodium deoxycholate and 0.1% sodium dodecylsulfate) supplemented with a protease inhibitor mixture was added to the resultant cell pellet deposit and lysis was performed on a shaker at 4° C. for 30 minutes. Then, the cell lysate was centrifuged at 12000× rpm for 10 minutes. M2 microbeads coupled with Flag antibody were added to the supernatant and incubation was performed overnight at 4° C. Then, the samples were centrifuged, washed three times with RIPA buffer, boiled in Laemmle buffer (Biorad, CA), and western blot analysis was performed using 8% SDS PAGE gel.

4. Western Blot Analysis

For Western blot analysis, cells were lysed at 4° C. or on ice for above 30 minutes using an appropriate volume of RIPA buffer (150 mM NaCl, 50 mM Tris-HCl, pH 7.4, 0.1% SDS, 1% TritonX-100, 1 mM EDTA, 1 mM PMSF, 1% sodium deoxycholate, 1 mM NaF, 1 mM $Na_3VO_4$, in deionized water). Centrifugation was performed at 12000× rpm for 10 minutes, and the supernatant was determined for the protein concentration using BCA kit (Thermo) and then 5× loading buffer was added and boiling was performed at 100° C. for 10 minutes. After a short centrifugation, the samples were separated by electrophoresis by 10% SDS-PAGE and transferred to a PVDF membrane, then blocked with 5% skimmed milk powder for above one hour, and then incubated with the primary antibody at the optimal concentration overnight at 4° C. The membrane was washed 3 times with 0.1% PBST (1×TBS, 0.1% Tween-20) for 10 minutes each time, and then incubated with the secondary antibody at room temperature for 1 hour. The signals were visualized by enhancing chemiluminescence.

5. Cell Growth Assay

According to the protocol provided by the manufacturer, the detection principle is that the succinate dehydrogenase in the mitochondria of living cells can reduce the exogenous MTT to water-insoluble blue-purple crystal formazan and deposit it in the cells, but dead cells do not have such a function. Dimethyl sulfoxide (DMSO) can dissolve formazan in cells, and its light absorption value measured at 570 nm wavelength with an enzyme-linked immunodetector can indirectly reflect the number of living cells. Cell growth was determined by 3-(4,5-dimethylthiazol-2-yl)-2,5-diphenyltetrazolium bromide (MTT) assay in a 96-well plate. Specifically, the cells were digested and counted, and then resuspended into a system containing 5000 cells per 200 µL of culture medium and seeded in each well of a 96-well plate. The next day, the medium was replaced with a medium containing different concentrations of sotagliflozin, apatinib, lenvatinib, and the composition of them. After 48 or 72 hours of incubation with the drugs, 20 µL of MTT reagent was added to each well and incubated for 2 hours. After discarding the medium, the formazan deposit in the cells was dissolved in 100 µL of DMSO. The absorbance was measured at 570 nm by a microplate reader. Samples were used in quadruplicate in each group.

6. Evaluation of the Efficacy on the Transplanted Tumor in Nude Mice

Hep3B cells were cultured with 10% serum DMEM medium and were digested and counted after they grew into the logarithmic phase. According to exploration of the preliminary conditions of the present invention, a transplanted tumor can be formed in about 21 days after 5*10e6 cells of Hep3B cells were inoculated subcutaneously in the armpit of Balbc nude mice (purchased from Beijing Vital River Laboratory Animal Technology Co., Ltd.). Therefore, the present invention adopted a dose of 5*10e6 cells per nude mouse, and administration was performed in groups after the tumors grew into an average volume of 100 $mm^3$ in about 21 days. The administration was divided into a solvent control group, an apatinib 50 mg/kg oral administration group, a sotagliflozin 20 mg/kg intraperitoneal injection group, and a combination group of simultaneous apatinib 50 mg/kg oral administration and sotagliflozin 20 mg/kg intraperitoneal injection. The administration cycle was once every other day, and the tumor volumes were measured every Tuesday and Friday and calculated according to the formula $V=a*b^2/2$ (a is the measured long diameter of the tumor, b is the measured short diameter of the tumor). A graph was mapped using Graphpad prism 5 and the measurement results were analyzed statistically.

7. Statistical Analysis

Student's t test was used to evaluate the differences in the growth of the cells and of the transplanted tumor in nude mice treated with the SGLT1 inhibitor or the VEGFR2 inhibitor such as sotagliflozin, apatinib, and lenvatinib of different concentrations under different combination conditions. A P value of less than 0.05 is defined as statistically significant.

8. Test Results

Figure 1C:
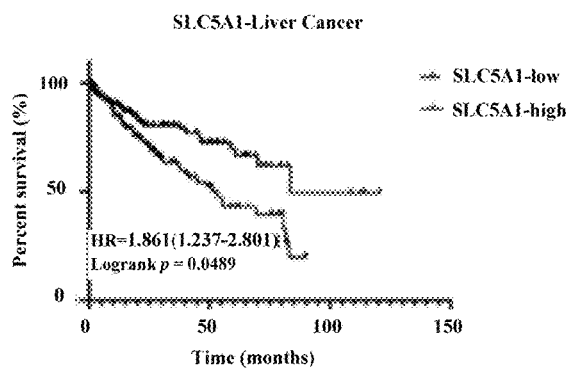
FIG. 1C is the relationship between high expression of SGLT1 and the prognosis of patients with liver cancer.
Figure 1D:
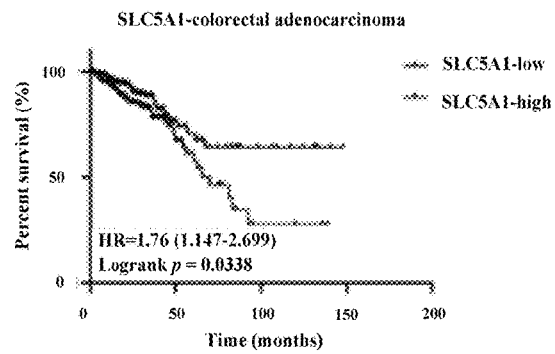
FIG. 1D is the relationship between high expression of SGLT1 and the prognosis of patients with colorectal adenocarcinoma.

FIG. 1: FIG. 1A and FIG. 1B conclude that the overall survival of patients with higher VEGFR2 expression is shorter by analyzing the correlation between the expression level of VEGFR2 in the cancer tissues of patients with liver cancer or colorectal adenocarcinoma and the overall survival of patients according to the TCGA database; FIG. 1C and FIG. 1D conclude that the overall survival of patients with higher SGLT1 expression is shorter by analyzing the correlation between the expression level of SGLT1 expression in the cancer tissues of patients with liver cancer or colorectal adenocarcinoma and the overall survival of the patients according to the TCGA database; it is proved that the high expression of VEGFR2 and SGLT1 is related to the poor prognosis of patients with either of these two cancers, indicating the relationship between the expression of the two in the tumor cells themselves and the prognosis.

Figure 2:
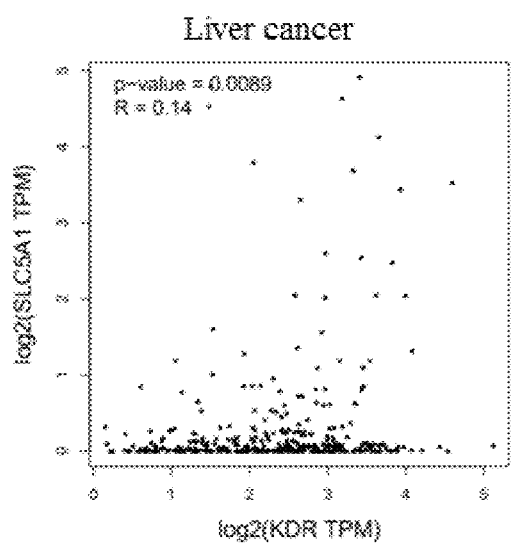
Figure 2:
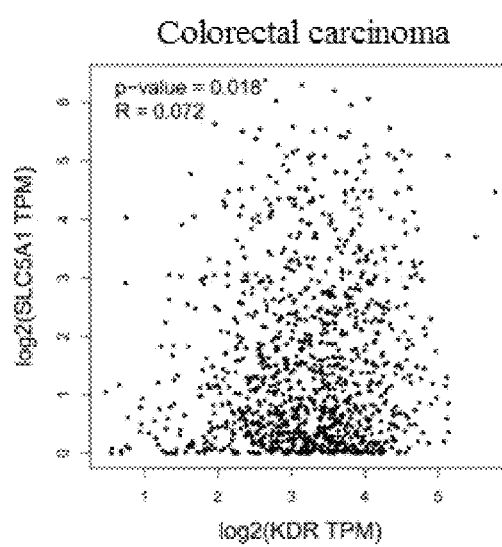
Figure 3:
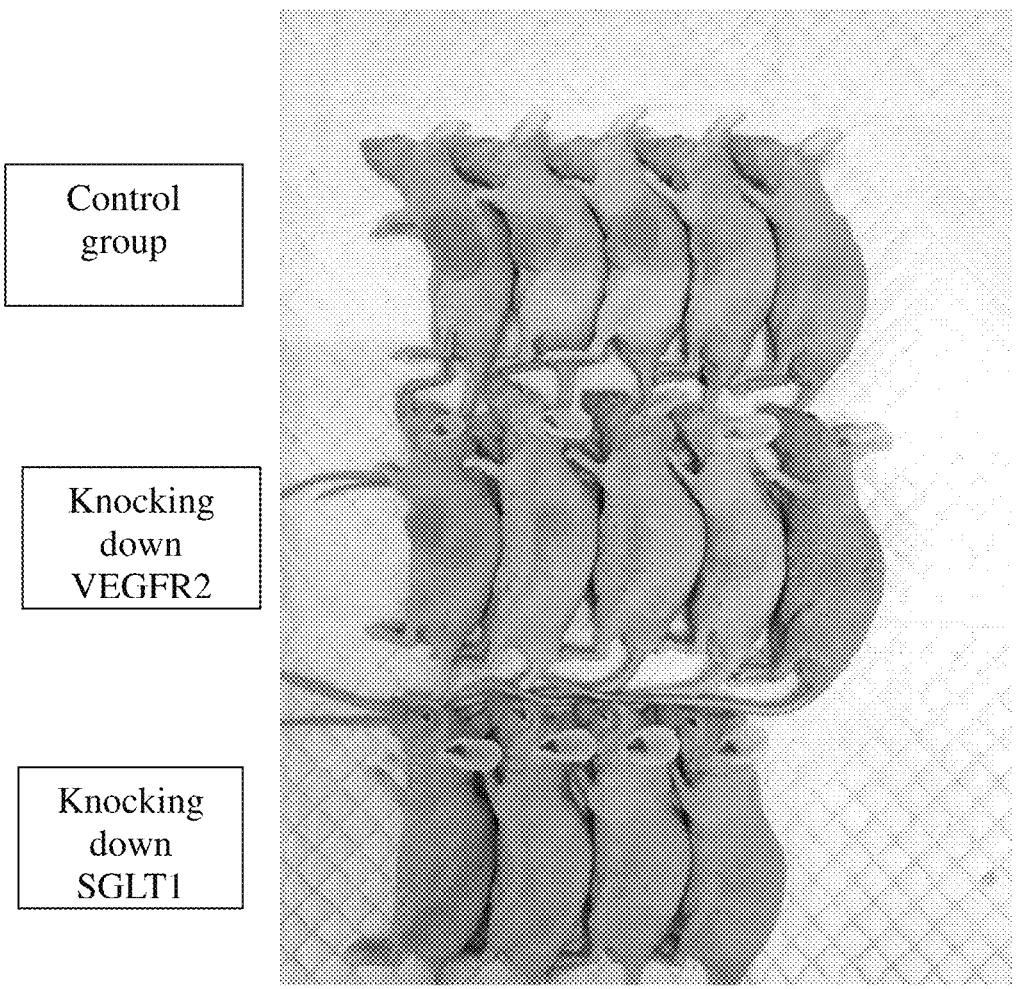
FIG. 3 shows that knockdown of VEGFR2 or SGLT1 in the hepatoma cell line damages the tumorigenicity of cells on nude mice.

FIG. 2: FIG. 2A further analyzes by using Pearson's test to show that in the TCGA database, the expression level of VEGFR2 in the cancer tissues of liver cancer patients has a positive correlation with that of SGLT1; FIG. 2B further analyzes by using Pearson's test to show that in the TCGA database, the expression level of VEGFR2 in the cancer tissues of colorectal adenocarcinoma patients has a positive correlation with that of SGLT1. It shows that the function of VEGFR2 and that of SGLT1 are likely to have a certain correlation.

FIG. 3: Knockdown of VEGFR2 or SGLT1 in the hepatoma cell line damages the tumorigenicity of cells on nude mice; it shows that the two genes VEGFR2 and SGLT1 play an important role in the development and progression of tumors.

FIG. 4: After knockdown of SGLT1, SGLT2 or VEGFR2 from the liver cancer cell line Hep3B using shRNA technology, changes in the intensity of the phosphorylation of ERK1/2 signaling pathway downstream of the VEGFR2 is detected using Western blot. Knockdown of SGLT1 and of VEGFR2 can consistently reduce the intensity of the phosphorylation of ERK1/2, while knockdown of SGLT2 has no such effect. It shows that knockdown of SGLT1 and of VEGFR2 will consistently induce the down-regulation of intensity of the phosphorylation of ERK1/2, while knockdown of SGLT2 has no such effect.

FIG. 5: After knockdown of SGLT1, SGLT2 or VEGFR2 from the liver cancer cell line Hep3B using shRNA technology, the cells of the control group and the cells in which VEGFR2, SGLT1 or SGLT2 is knocked down are treated with the VEGFR2 inhibitor apatinib respectively for the detection of the growth inhibition of different concentrations of apatinib on each cell line, and the half maximal inhibitory concentration IC50 value is calculated; knockdown of SGLT1 and of VEGFR2 can consistently reduce the IC50 value of apatinib, while knockdown of SGLT2 has no such effect.

FIG. 6: After knockdown of SGLT1, SGLT2, or VEGFR2 from the liver cancer cell line Hep3B using shRNA technology, the cells of the control group and the cells in which VEGFR2, SGLT1 or SGLT2 is knocked down are treated with low-glucose DMEM medium respectively for the detection of the tolerance of each cell line to glucose starvation. Knockdown of VEGFR2 and of SGLT1 can consistently reduce the tolerance of cells to glucose starvation, but knockdown of SGLT2 has no significant effect.

FIG. 7: There is an interaction between VEGFR2 and SGLT1 proteins; the FLAG-tagged SGLT1 and the untagged VEGFR2 vector were co-transfected into 293T cells using immunoprecipitation method, the cells were lysed after 24 hours, and FLAG beads were added for binding for 5 hours, Western blot detection was performed using VEGFR2 antibody and Flag antibody. The results show that there is an interaction between VEGFR2 and SGLT1 proteins.

FIG. 8: The liver cancer cell line HepG2 is treated with the VEGFR2 inhibitor and the SGLT1 inhibitor, and the IC50 values of the VEGFR2 inhibitor and the SGLT1 inhibitor used as single agents or a composition of the two in different doses are measured using MTT method. It is proved that the composition has a significant inhibitory effect on liver cancer cell lines.

Figure 9A:
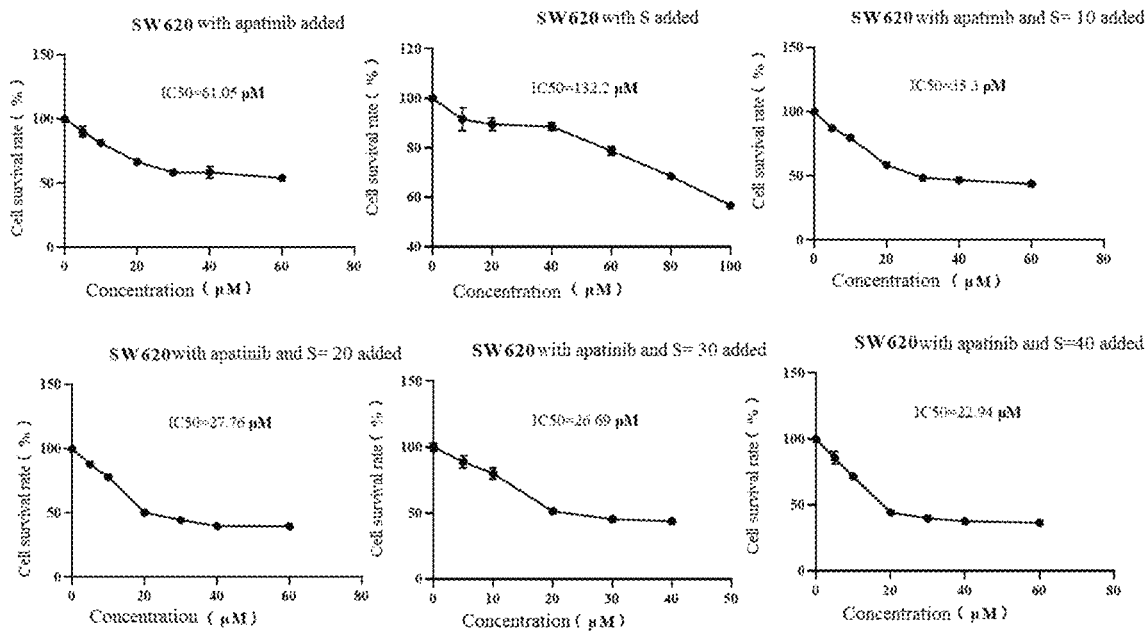
FIG. 9a shows the treatment of the colorectal adenocarcinoma cell line SW620 with the VEGFR2 inhibitor and the SGLT1 inhibitor.
Figure 9B:
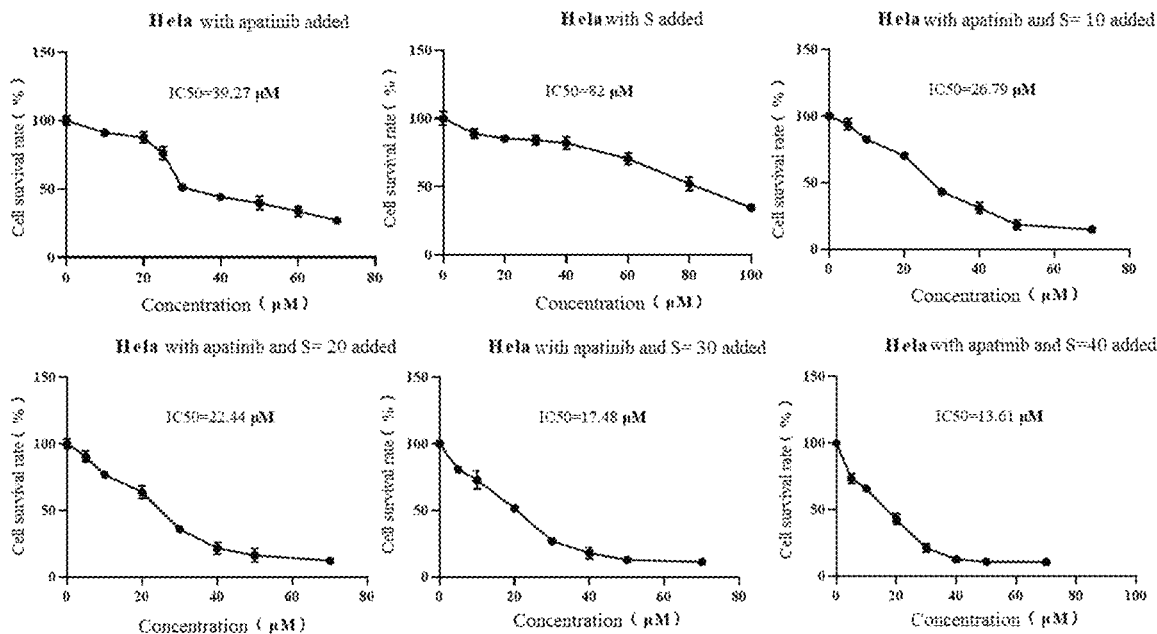
FIG. 9b shows the treatment of the cervical cancer cell line HeLa with the VEGFR2 inhibitor and the SGLT1 inhibitor.
Figure 9C:
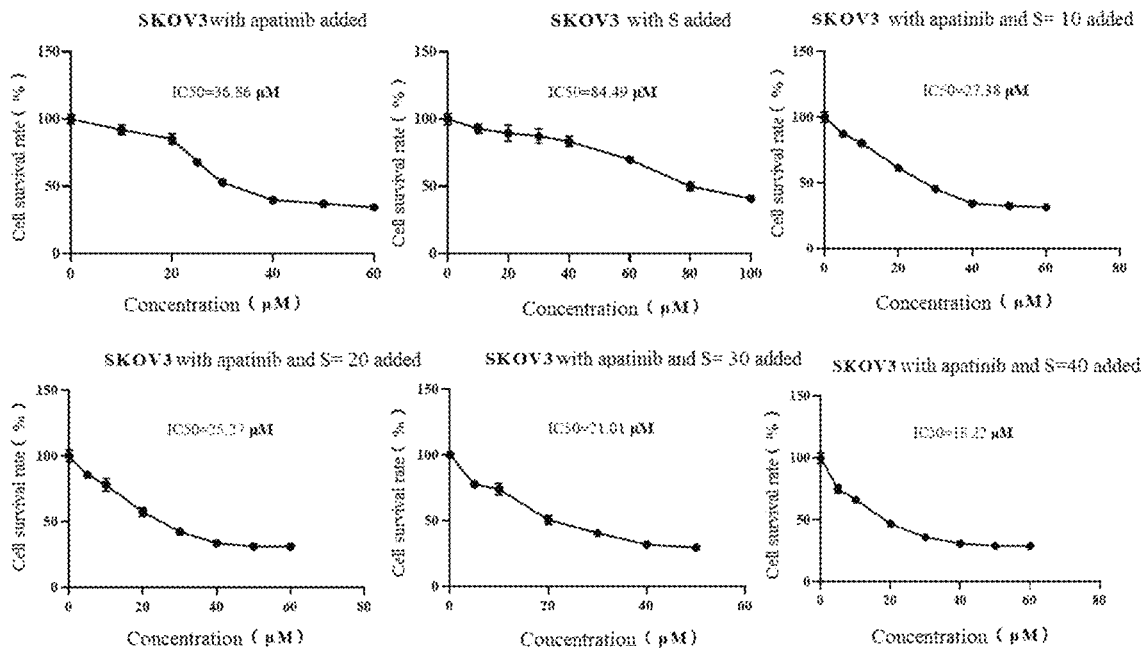
FIG. 9c shows the treatment of the ovarian cancer cell line SKOV3 with the VEGFR2 inhibitor and the SGLT1 inhibitor.
Figure 9D:
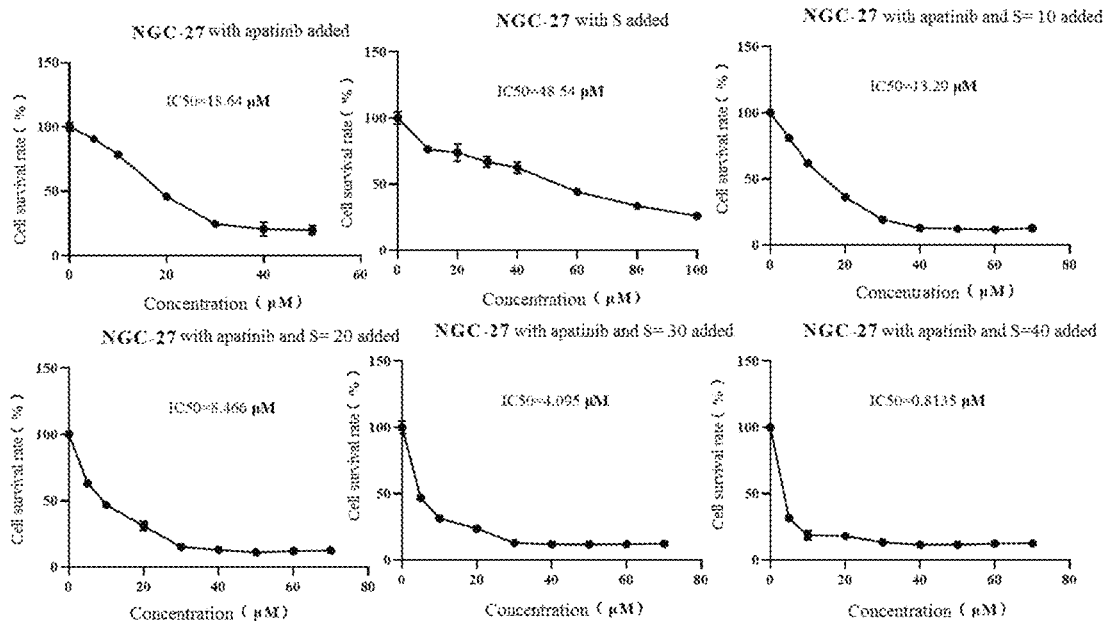
FIG. 9d shows the treatment of the gastric cancer cell line NGC27 with the VEGFR2 inhibitor and the SGLT1 inhibitor.
Figure 9E:
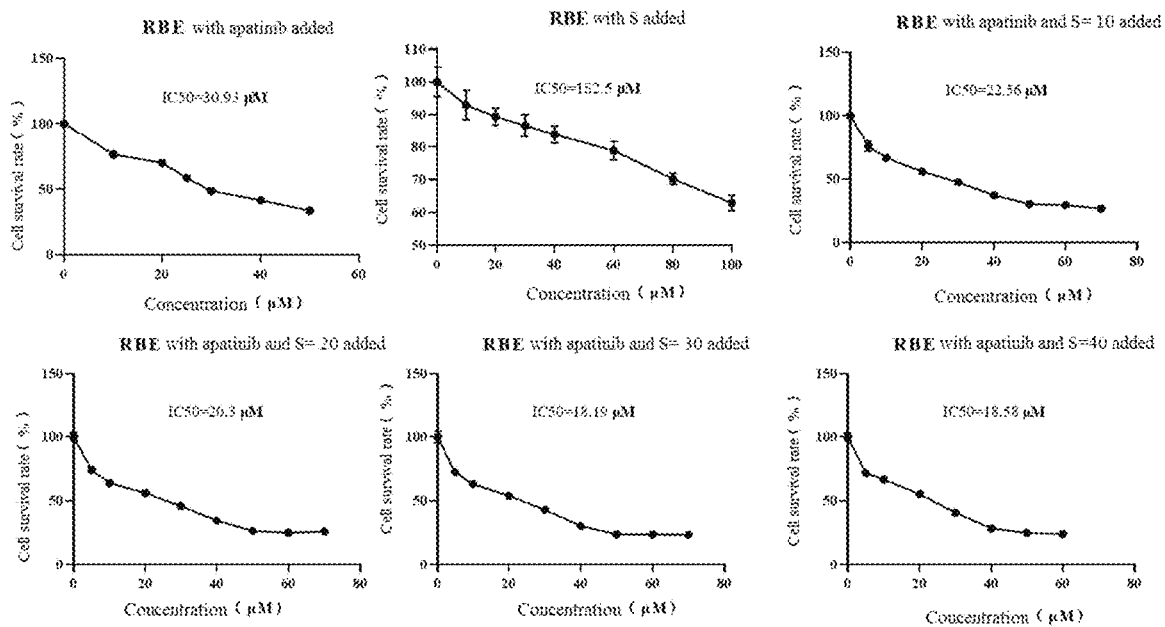
FIG. 9e shows the treatment of the cholangiocarcinoma cell line RBE with the VEGFR2 inhibitor and the SGLT1 inhibitor.
Figure 9F:
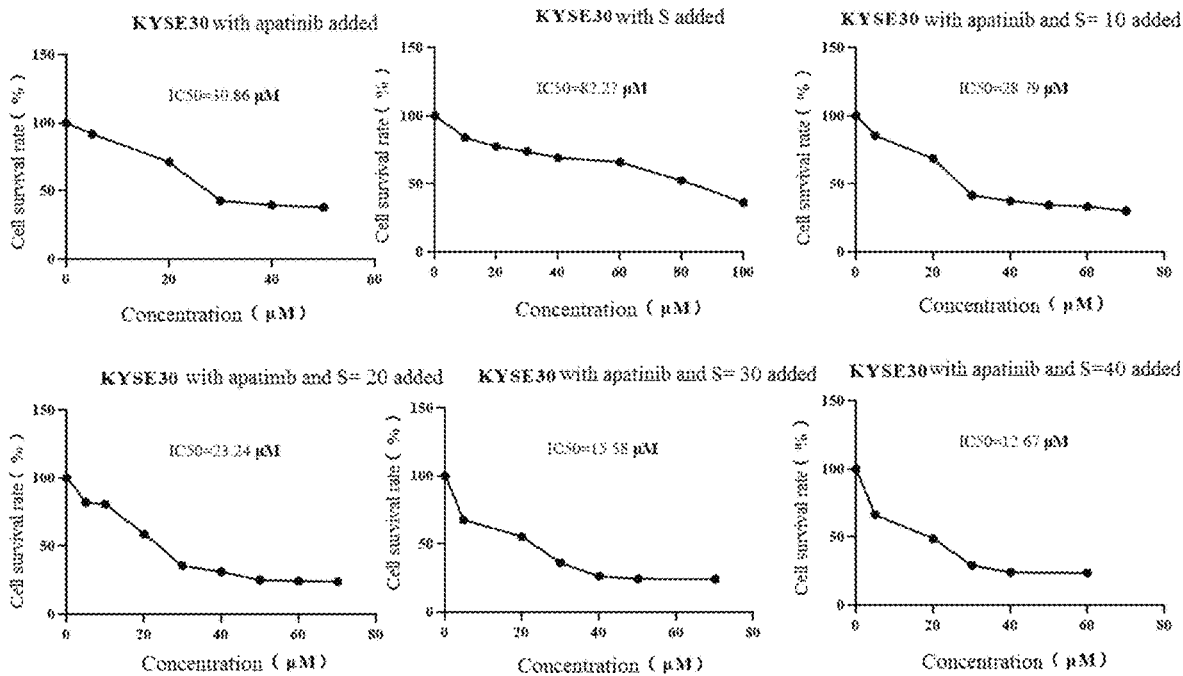
FIG. 9f shows the treatment of the esophageal cancer cell line KYSE30 with the VEGFR2 inhibitor and the SGLT1 inhibitor.
Figure 10A:
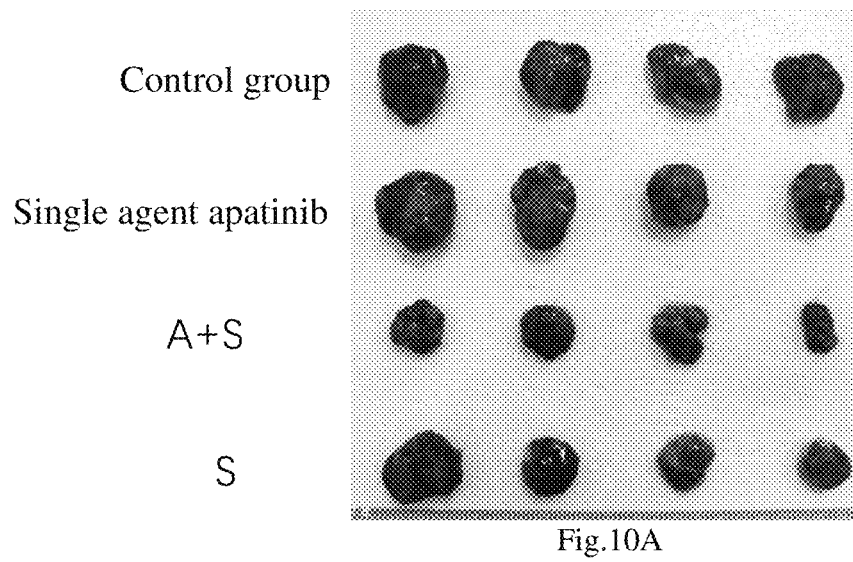
FIG. 10A is a macroscopic view of the tumors of each group after the end of the administration.
Figure 10B:
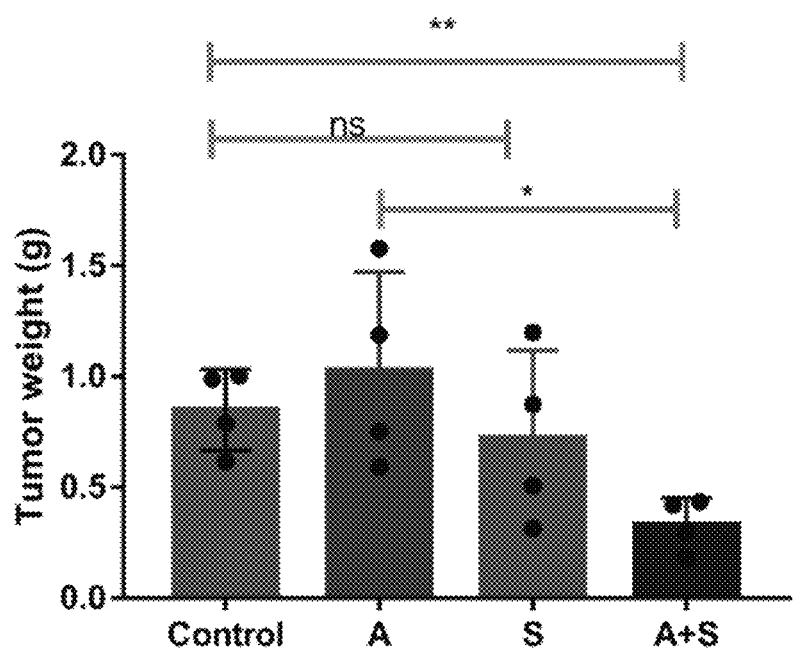
FIG. 10B is the weight of the tumors of each group after the end of the administration.

FIG. 9: FIG. 9a shows the treatment of the colorectal adenocarcinoma cell line SW620 with the VEGFR2 inhibitor and the SGLT1 inhibitor; FIG. 9b shows the treatment of the cervical cancer cell line HeLa with the VEGFR2 inhibitor and the SGLT1 inhibitor; FIG. 9c shows the treatment of the ovarian cancer cell line SKOV3 with the VEGFR2 inhibitor and the SGLT1 inhibitor; FIG. 9d shows the treatment of the gastric cancer cell line NGC27 with the VEGFR2 inhibitor and the SGLT1 inhibitor; FIG. 9e shows the treatment of the cholangiocarcinoma cell line RBE with the VEGFR2 inhibitor and the SGLT1 inhibitor; FIG. 9f shows the treatment of the esophageal cancer cell line KYSE30 with the VEGFR2 inhibitor and the SGLT1 inhibitor; it is proved that the composition has a significant inhibitory effect on colorectal adenocarcinoma cell line, cervical cancer cell line, ovarian cancer cell line, gastric cancer cell line, cholangiocarcinoma cell line, and esophagus cancer cell line.

FIG. 10: The transplanted tumor of the liver cancer cell line Hep3B in nude mice is treated using the VEGFR2 inhibitor and the SGLT1 inhibitor, and the inhibitory effect of the VEGFR2 inhibitor (50 mg/kg) and the SGLT1 inhibitor (20 mg/kg) used as single agents or a composition thereof on tumor growth is detected. It is proved that the composition has a significant inhibitory effect on tumor growth.

Example 2

Figures 11, 12:
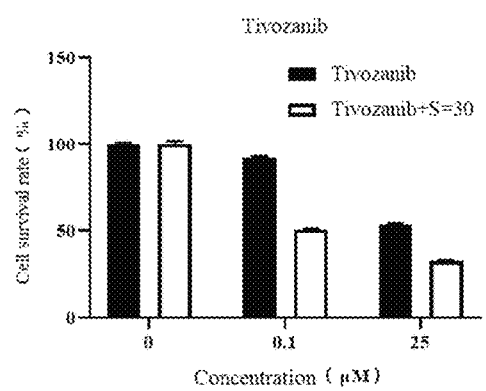
Figures 11, 12, 13:
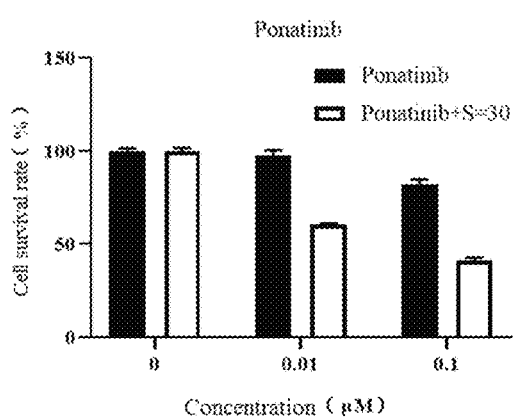
Figures 11, 12, 13, 14:
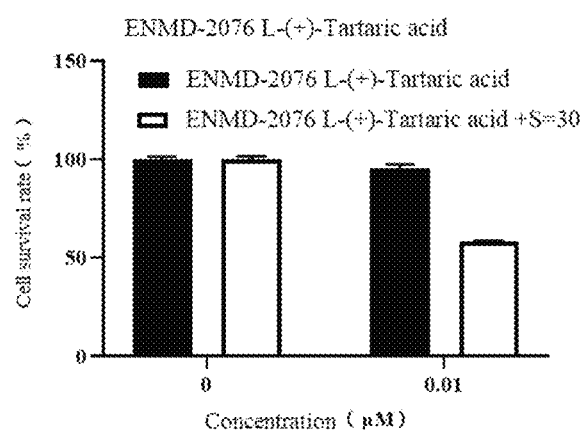
Figures 11, 12, 13, 14, 15:
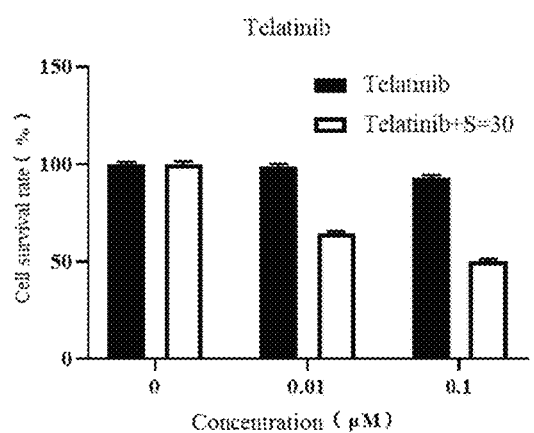
Figures 11, 12, 13, 14, 15, 16:
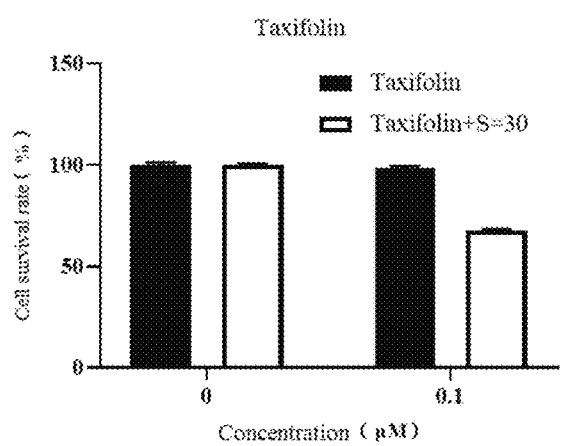
Figures 11, 12, 13, 14, 15, 16, 17:
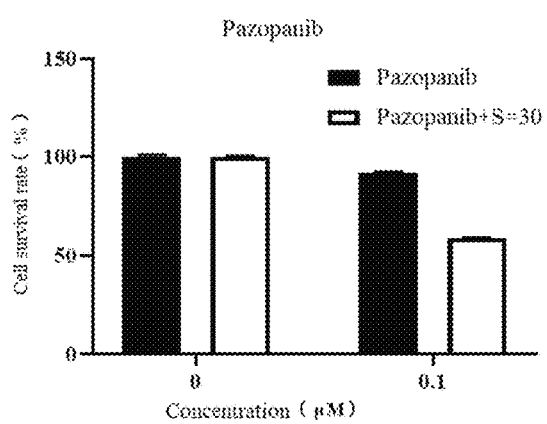
Figures 11, 12, 13, 14, 15, 16, 17, 18:
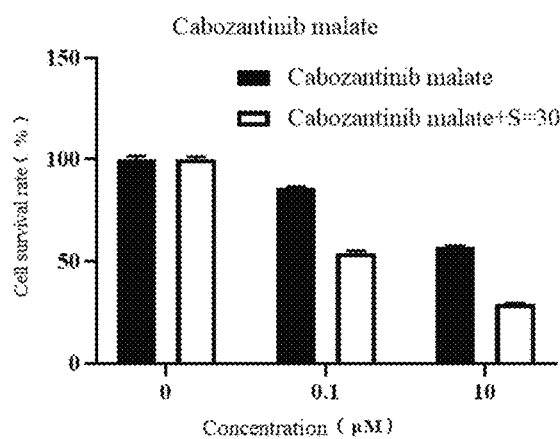
Figures 11, 12, 13, 14, 15, 16, 17, 18, 19:
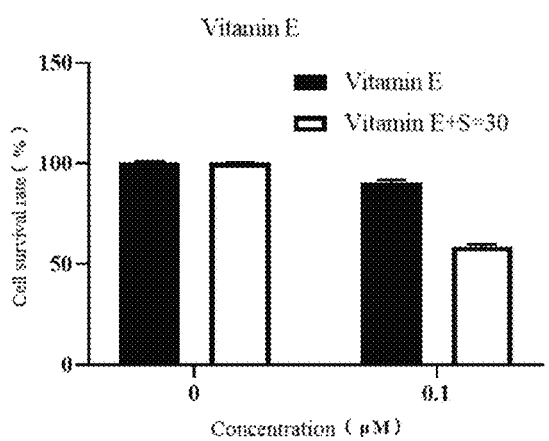
Figures 11, 12, 13, 14, 15, 16, 17, 18, 19, 20:
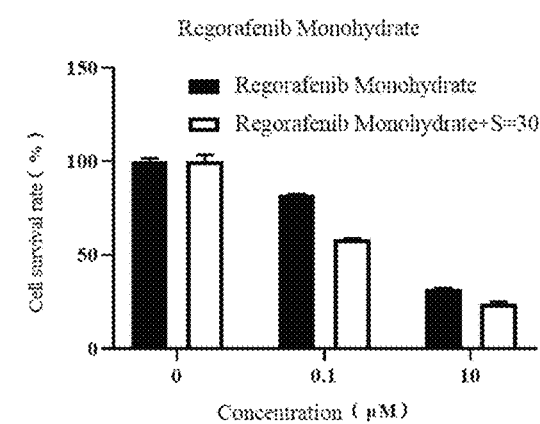
Figures 11, 12, 13, 14, 15, 16, 17, 18, 19, 20, 21:
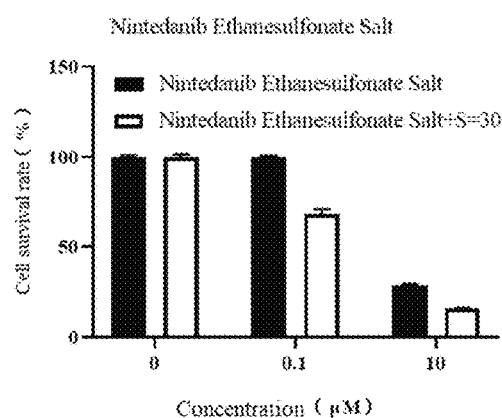
Figures 11, 12, 13, 14, 15, 16, 17, 18, 19, 20, 21, 22:
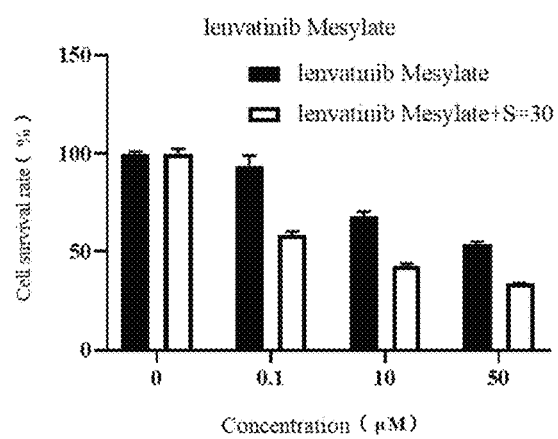
Figures 11, 12, 13, 14, 15, 16, 17, 18, 19, 20, 21, 22, 23:
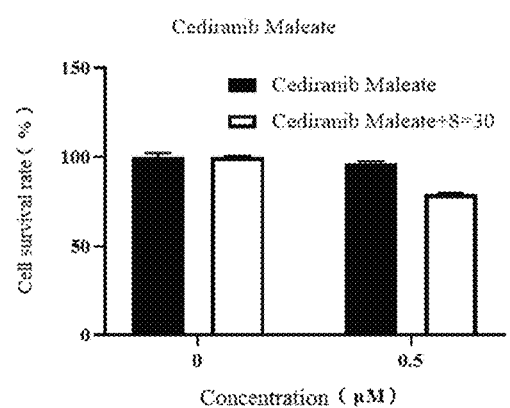
Figures 11, 12, 13, 14, 15, 16, 17, 18, 19, 20, 21, 22, 23, 24:
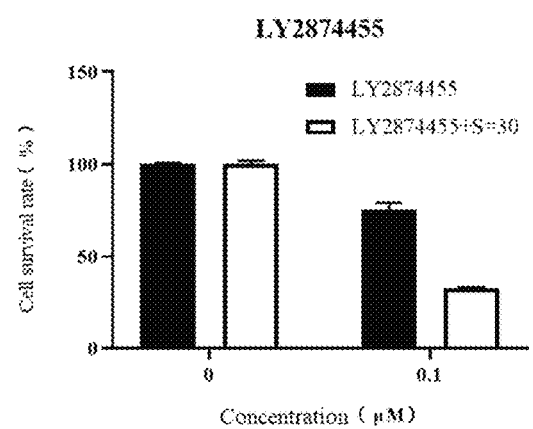
Figures 11, 12, 13, 14, 15, 16, 17, 18, 19, 20, 21, 22, 23, 24, 25:
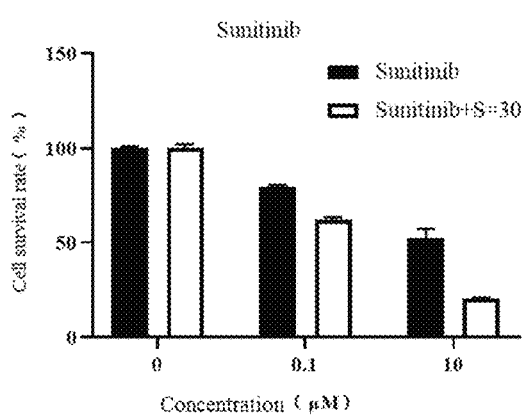
Figures 11, 12, 13, 14, 15, 16, 17, 18, 19, 20, 21, 22, 23, 24, 25, 26:
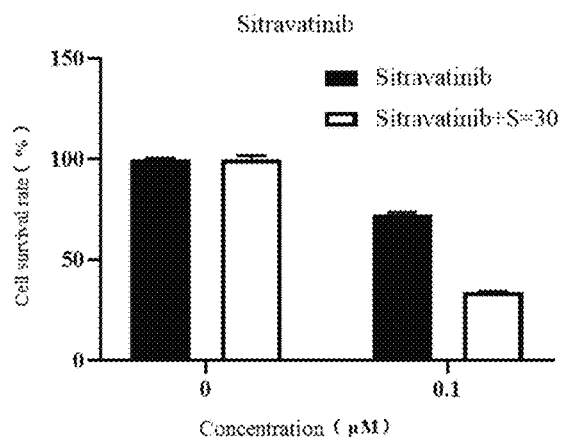
Figures 11, 12, 13, 14, 15, 16, 17, 18, 19, 20, 21, 22, 23, 24, 25, 26, 27:
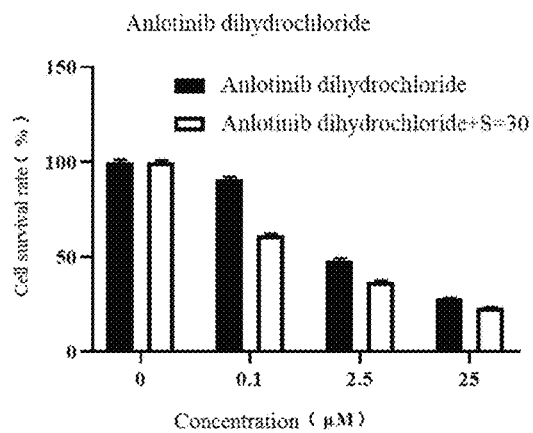
Figures 11, 12, 13, 14, 15, 16, 17, 18, 19, 20, 21, 22, 23, 24, 25, 26, 27, 28:
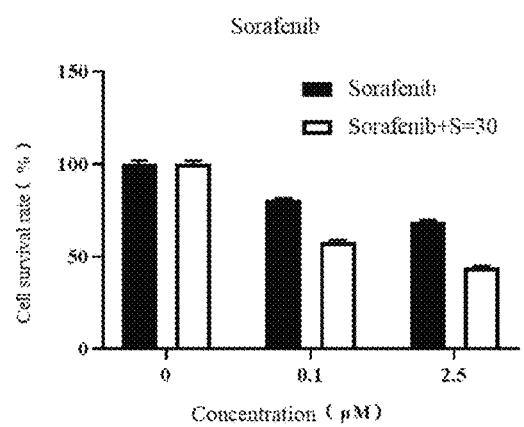
Figures 11, 12, 13, 14, 15, 16, 17, 18, 19, 20, 21, 22, 23, 24, 25, 26, 27, 28, 29:
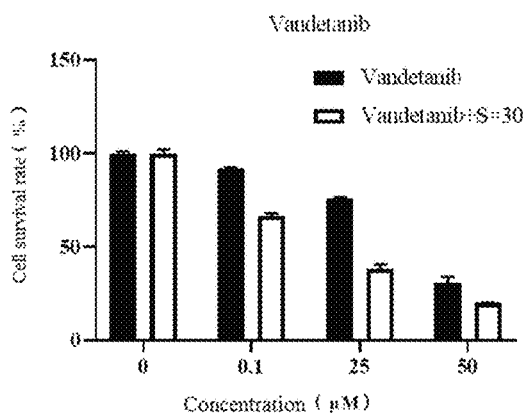
Figures 11, 12, 13, 14, 15, 16, 17, 18, 19, 20, 21, 22, 23, 24, 25, 26, 27, 28, 29, 30:
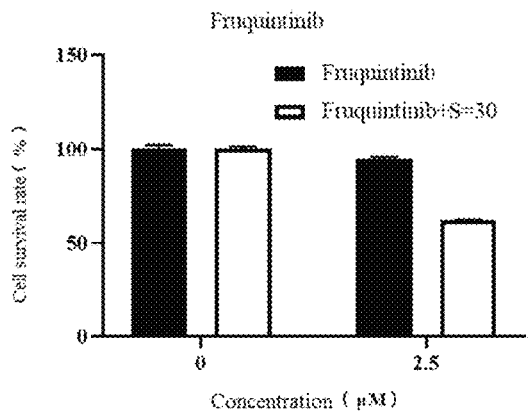

In FIG. 8, FIG. 9 and FIG. 10, the VEGFR2 inhibitor represented by apatinib used in combination with the SGLT1 inhibitor has in vitro and in vitro efficacy. The present invention further verifies the effect of using all VEGFR2 inhibitors in combination with the SGLT1 inhibitor that have completed clinical trials and are undergoing clinical trials using the liver cancer cell line. The results showed that when used in combination with the SGLT1 inhibitor, the drugs such as axitinib (FIG. 11-1), nintedanib (BIBF1120) (FIG. 11-2), cediranib (AZD2171) (FIG. 11-3), pazopanib HCl (GW786034 HCl) (FIG. 11-4), sunitinib malate (FIG. 11-5), brivanib (BMS-540215) (FIG. 11-6), cabozantinib (XL184, BMS-907351) (FIG. 11-7), brivanib alaninate (BMS-582664) (FIG. 11-8), lenvatinib (E7080) (FIG. 11-9), regorafenib (BAY 73-4506) (FIG. 11-10), ENMD-2076 (FIG. 11-11), tivozanib (AV-951) (FIG. 11-12), ponatinib (AP24534) (FIG. 11-13), ENMD-2076 L-(+)-tartaric acid (FIG. 11-14), telatinib (FIG. 11-15), taxifolin (dihydroquercetin) (FIG. 11-16), pazopanib (FIG. 11-17), cabozantinib malate (XL184) (FIG. 11-18), vitamin E (FIG. 11-19), regorafenib monohydrate (FIG. 11-20), nintedanib ethanesulfonate salt (FIG. 11-21), lenvatinib mesylate (FIG. 11-22), cediranib maleate (FIG. 11-23), 4-[(1E)-2-[5-[(1R)-1-(3,5-dichloro-4-pyridyl)ethoxy]-1H-indazol-3-yl]vinyl]-1H-pyrazole-1-etha nol (LY2874455) (FIG. 11-24), sunitinib (FIG. 11-25), sitravatinib (MGCD516) (FIG. 11-26), anlotinib (AL3818) dihydrochloride (FIG. 11-27), sorafenib (FIG. 11-28), vandetanib (FIG. 11-29) and fruquintinib (FIG. 11-30) have better tumor suppressive effect than as a single agent.

Conclusions

The present invention finds that there is an interaction between SGLT1 and VEGFR2, and this interaction plays an important role in each other's functions. Knockdown of VEGFR2 will affect not only the proliferation of tumor cells and the transduction of growth signals, but also the function of SGLT1. On the other hand, knockdown of SGLT1 will affect not only the survival of cancer cells under low-glucose conditions, but also the VEGFR2 signaling pathway and cell proliferation. Therefore, the composition consisting of the VEGFR2 inhibitor and the SGLT1 inhibitor has a significant inhibitory effect on tumor growth, and has a significant synergistic effect on tumor suppression.

The above mentioned are only the preferred embodiments of the present invention. It should be pointed out that for those of ordinary skill in the art, several improvements and modifications can be made without departing from the principle of the present invention, and these improvements and modifications should also be regarded to fall within the protection scope of the present invention.

The invention claimed is:

1. A composition comprising a sodium/glucose co-transporter 1 inhibitor and a vascular endothelial growth factor receptor 2 inhibitor, wherein the sodium/glucose co-transporter 1 inhibitor is sotagliflozin; and wherein the vascular endothelial growth factor receptor 2 inhibitor is selected from at least one of apatinib, axitinib, nintedanib, cediranib, pazopanib hydrochloride, sunitinib malate, brivanib, cabozantinib, brivanib alaninate, lenvatinib, regorafenib, ENMD-2076, ENMD-2076 L-(+)-tartaric acid, tivozanib, ponatinib, fruquintinib, telatinib, taxifolin, pazopanib, cabozantinib malate, vitamin E, regorafenib monohydrate, nintedanib ethanesulfonate salt, lenvatinib mesylate, cediranib-maleate, 4-[(1E)-2-[5-[(1R)-1-(3,5-dichloro-4-pyridyl)ethoxyl-1H-indazol-3-yl]vinyl]-1H-pyrazole-1-ethanol, sunitinib, sitravatinib, anlotinib dihydrochloride, sorafenib, vandetanib and a monoclonal antibody medicament targeting vascular endothelial growth factor receptor; wherein the sodium/glucose co-transporter 1 inhibitor is at a dosage of 1 to 100 mg/kg and the vascular endothelial growth factor receptor 2 inhibitor is at a dosage of 10 to 500 mg/kg.

2. The composition according to claim 1, wherein the sodium/glucose co-transporter 1 inhibitor is administered at a dosage of 10 to 50 mg/kg.

3. The composition according to claim 1, wherein the vascular endothelial growth factor receptor 2 inhibitor is administered at a dosage of 10 to 100 mg/kg.

4. A method for treating cancer, comprising administering a therapeutically effective amount of the composition according to claim 1 to a subject in need thereof;
wherein the cancer is selected from one or more of breast cancer, cervical cancer, colorectal cancer, esophageal cancer, cholangiocarcinoma, liver cancer, ovarian cancer, and gastric cancer.

5. A medicament for treating cancer comprising the composition according to claim 1;
wherein the cancer is selected from one or more of breast cancer, cervical cancer, colorectal cancer, esophageal cancer, cholangiocarcinoma, liver cancer, ovarian cancer, and gastric cancer.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial
<220> FEATURE:
<223> OTHER INFORMATION: Sglt1-1 shRNA targeting sequence

<400> SEQUENCE: 1
aggagagcct atgacctatt t                                              21

<210> SEQ ID NO 2
<211> LENGTH: 21
<212> TYPE: DNA
<213> ORGANISM: Artificial
<220> FEATURE:
<223> OTHER INFORMATION: Sglt1-2 shRNA targeting sequence

<400> SEQUENCE: 2
gcctgatgct atcagtcatg c                                              21

<210> SEQ ID NO 3
<211> LENGTH: 21
<212> TYPE: DNA
<213> ORGANISM: Artificial
<220> FEATURE:
<223> OTHER INFORMATION: Sglt2-1 shRNA targeting sequence

<400> SEQUENCE: 3
gcatatttcc tgctggtcat t                                              21

<210> SEQ ID NO 4
<211> LENGTH: 21
<212> TYPE: DNA
<213> ORGANISM: Artificial
<220> FEATURE:
<223> OTHER INFORMATION: Sglt2-2 shRNA targeting sequence

<400> SEQUENCE: 4
ggtcatcacg atgccacagt a                                              21

<210> SEQ ID NO 5
<211> LENGTH: 21
<212> TYPE: DNA
<213> ORGANISM: Artificial
<220> FEATURE:
<223> OTHER INFORMATION: Vegfr2-1 shRNA targeting sequence

<400> SEQUENCE: 5
gatgaaagtt accagtctat t                                              21

<210> SEQ ID NO 6
<211> LENGTH: 21
<212> TYPE: DNA
```

```
<213> ORGANISM: Artificial
<220> FEATURE:
<223> OTHER INFORMATION: Vegfr2-2 shRNA targeting sequence

<400> SEQUENCE: 6
gctgacatgt acggtctatg c                                              21
```